(12) United States Patent
Ghosh et al.

(10) Patent No.: US 10,551,283 B2
(45) Date of Patent: Feb. 4, 2020

(54) ACTIVELY SHAKEN IN-SITU PASSIVE SAMPLING DEVICE

(71) Applicant: University of Maryland, Baltimore County, Baltimore, MD (US)

(72) Inventors: Upal Ghosh, Ellicott City, MD (US); Mehregan Jalalizadeh, Huntington Beach, CA (US)

(73) Assignee: UNIVERSITY OF MARYLAND, BALTIMORE COUNTY, Baltimore, MD (US)

( * ) Notice: Subject to any disclaimer, the term of this patent is extended or adjusted under 35 U.S.C. 154(b) by 93 days.

(21) Appl. No.: 15/718,119

(22) Filed: Sep. 28, 2017

(65) Prior Publication Data
US 2018/0088008 A1    Mar. 29, 2018

Related U.S. Application Data

(60) Provisional application No. 62/401,366, filed on Sep. 29, 2016.

(51) Int. Cl.
| | | |
|---|---|---|
| *G01N 1/10* | (2006.01) | |
| *G01N 1/40* | (2006.01) | |
| *G01N 33/18* | (2006.01) | |

(52) U.S. Cl.
CPC ............. *G01N 1/10* (2013.01); *G01N 1/4055* (2013.01); *G01N 33/1826* (2013.01); *G01N 2001/1025* (2013.01); *G01N 2001/4061* (2013.01)

(58) Field of Classification Search
CPC .......... G01N 1/10; G01N 1/00; G01N 1/2214; G01N 1/2202; G01N 1/22; G01N 1/02

USPC ........................................................ 436/140
See application file for complete search history.

(56) References Cited

U.S. PATENT DOCUMENTS

| | | |
|---|---|---|
| 2011/0070597 A1 | 3/2011 | Vlahos et al. |
| 2017/0115265 A1 | 4/2017 | Conder |

OTHER PUBLICATIONS

Ghosh, Upal et al, Actively Shaken In-Situ Passive Sampler Platform for Methylmercury and Organics, SERDP Project ER-2540, SERDP, Feb. 2016, pp. 1-122. (Year: 2016).*
Jalalizadeh, Mehregan et al, In Situ Passive Sampling of Sediment Porewater Enhanced by Periodic Vibration, Environ. Sci. Technol. 2016, 50, 8741-8749. (Year: 2016).*
Jalalizadeh, Mehregan et al, Supporing Information, In Situ Passive Sampling of Sediment Porewater Enhanced by Periodic Vibration, Environ. Sci. Technol. 2016, 50, 8741-8749. (Year: 2016).*
Apell, J. N., Gschwend, P. M. Validating the use of performance reference compounds in passive samplers to assess porewater concentrations in sediment beds. Environ. Sci. Technol. 2014, 48. 10301-10307.

(Continued)

*Primary Examiner* — Christine T Mui
(74) *Attorney, Agent, or Firm* — Tristan A. Fuierer; Olive Law Group, PLLC

(57) ABSTRACT

A vibrating platform for the deploying of passive sampling devices in sediments and other media to be sampled. The vibrating platform can greatly enhance the rate of mass transfer of analytes, such as polycyclic aromatic hydrocarbons and polychlorinated biphenyls, into passive sampler material by disrupting the formation of a depletion layer in proximity of the passive sampler material.

20 Claims, 15 Drawing Sheets

(56) References Cited

OTHER PUBLICATIONS

Arp. H. P. H., Hale, S. E., Elmquist Krusa, M., Cornelissen, G., Grabanski, C. B., Miller, D. J., Hawthorne. S. B. Review of polyoxymethylene passive sampling methods for quantifying freely dissolved porewater concentrations of hydrophobic organic contaminants. Environ. Toxicol. Chem. 2015, 34, 710¬720.
Beckingham, B., Ghosh, U. Field-scale reduction of PCB bioavailability with activated carbon amendment to river sediments Environ. Sci. Technol. 2011, 45 (24) 10567-10574.
Booij. K., Hoedemaker, J. R., Bakker. J. F. Dissolved PCBs, PAHs, and HCB in Pore Waters and Overlying Waters of Contaminated Harbor Sediments. Environ. Sci. Technol. 2003, 37 (18), 4213-4220.
Booij, K., Smedes, F. An improved method for estimating in situ sampling rates of nonpolar passive samplers. Environ.. Sci. Technol. 2010, 44, 6789-6794.
Booij, K., Robinson, C.D., Burgess, R.M., Mayer, P., Roberts, C.A., Ahrens, L., Allan. LI., Brant, J. Jones, L., Kraus, U. R., Larsen, M.M., Lepom. P., Petersen, J., Profrock, D., Roose, P., Schafer, S., Smedes, F., Tixier, C., Vorkamp, K., Whitehouse, P. Passive Sampling in Regulatory Chemical Monitoring of Nonpolar Organic Compounds in the Aquatic Environment. Environ. Sci. Technol. 2015. 50, 3-17.
Cornelissen, G., Van Noort, P. C. M., Govers, H. A. J. Desorption kinetics of chlorobenzenes, polycyclic aromatic hydrocarbons, and polychlorinated biphenyls: Sediment extraction with Tenax and effects of contact time and solute hydrophobicity Environ. Toxicol. Chem. 1997, 16, 1351-1357.
Crank, J. The Mathematics of Winston, 2"d ed.; Oxford University Press: Oxford, 1975; p. 414.
Fernandez, L. A., Harvey, C. F. and Gschwend, P. M. Using Performance Reference Compounds in Polyethylene Passive Samplers to Deduce Sediment Porewater Concentrations for Numerous Target Chemicals. Environ. Sci. Technol. 2009, 43, 8888-8894.
Fernandez, L. A., Lao, W., Maruya, K. A., Burgess, R. M. Calculating the Diffusive Flux of Persistent Organic Pollutants between Sediments and the Water Column on the Palos Verdes Shelf Superfund Site Using Polymeric Passive Samplers. Environ. Sci. Technol. 2014.48 (7), 3925-3934.
Ghosh, U., Talley, J. W., Luthy, R. G. Particle-scale investigation of PAH desorption kinetics and thermodynamics from sediment Environ. Sci. Technol. 2001, 35, 3468-3475.
Ghosh, U., Zimmerman, J. R., and Luthy, R. G. PCB and PAH Speciation among Particle Types in Contaminated Harbor Sediments and Effects on PAH Bioavailability. Environ. Sci. Technol. 2003. 37. 2209-2217.
Ghosh, U., Kane Driscoll, S., Burgess, R. M., Jonker, M. T. O., Reible, D., Gobas, F., Choi, Y., Apitz, S. E., Maruya, K. A., Gala, W. R., Mortimer, M. and Beegan, C. Passive sampling methods for contaminated sediments: Practical guidance for selection, calibration, and implementation: Integr Environ Assess Manag. 2014, 10, 210-223.
Hawthorne, S. B., Grabanski, C. B., Miller, D. J. Measured partitioning coefficients for parent and alkyl polycyclic aromatic hydrocarbons in 114 historically contaminated sediments: Part 1. KOC values. Environ. Toxicol. Chem. 2006, 25, 2901-2911.

Huckins, J. N., Petty, J. D., Lebo, J. A., Almeida, F. V., Booij, K., Alvarez, D. A., Clark, R. C., Mogensen, B. B. Development of the permeability/performance reference compound approach for in situ calibration of semipermeable membrane devices. Environ. Sci. Technol. 2002, 36 (1), 85-91.
Huckins, J. N., Petty J. D., Booij, K. Monitors of Organic Chemicals in the Environment; Springer: New York, NY, 2006.
Khalil. M. F., Ghosh, U. and Kreitinger, J. P. Role of Weathered Coal Tar Pitch in the Partitioning of Polycyclic Aromatic Hydrocarbons in Manufactured Gas Plant Site Sediments. Environ. Sci. Technol. 2006, 40, 5681-5687.
Lampert, D. An assessment of the design of in situ management approaches for contaminated sediments. Ph.D. Thesis, The University of Texas at Austin, May 2010.
Lohmann, R. Critical Review of Low-Density Polyethylene's Partitioning and Diffusion Coefficients for Trace Organic Contaminants and Implications for Its Use as a Passive Sampler. Environ. Sci. Technol. 2011, 46, 606-618.
Mayer, P., Tolls, J., Hermens, J. L. M. and Mackay, D. Equilibrium Sampling Devices. Environ. Sci. Technol. 2003, 37, 184A-191A.
Mayer, P., Parkerton, T. F., Adams, R. G., Cargill, J. G., Gan, J., Gouin, T., Gschwend, P. M., Hawthorne, S. B., Helm, P., Witt, G., You, J. and Escher, B. I. Passive sampling methods for contaminated sediments: Scientific rationale supporting use of freely dissolved concentrations. Integr Environ Assess Manag. 2014, 10, 197-209.
Oen, A. M. P., Janssen, E. M. L., Cornelissen, G., Breedveld, G. D., Eek, E. and Luthy, R. G. In Situ Measurement of PCB Pore Water Concentration Profiles in Activated Carbon-Amended Sediment Using Passive Samplers. Environ. Sci. Technol. 2011, 45, 4053-4059.
Tcaciuc, A. P., Apell, J. N., Gschwend, P. M. Performance Reference Compound Calculator for Use in Support of PE Passive Samplers. http://www.serdp.org/Program-Areas/Environmental-Restoration/Contaminated-Sediments/ER-200915 (accessed May 30, 2017).—Cant Locate Reference.
Thompson, J., Hsieh, C., and Luthy, R. G. Modeling Uptake of Hydrophobic Organic Contaminants into Polyethylene Passive Samplers. Environ. Sci. Technol. 2015, 49 (4), 2270-2777.
Tomaszewski, J., Lutly, R. G. Field deployment of polyethylene devices to measure PCB concentrations in pore water of contaminated sediment. Environ. Sci. Technol. 2008, 42 (16), 6086-6091.
United States Environmental Protection Agency. Equilibrium Partitioning Sediment Benchmarks (ESBs) for the Protection of Benthic Organisms: Procedures for the Determination of the Freely Dissolved Interstitial Water Concentrations of Nonionic Organics. EPA-600-R-02-012. Office of Research and Development, Washington, DC, USA, 2012.
Jalalizadeh, Mehregan, "Analysis of Measurement Errors in Passive Sampling of Porewater PCB Concentrations under Static and Periodically Vibrated Conditions," Environ. Sci. Technol., 2017, pp. 7018-7027, vol. 51.
Jalalizadeh, Mehregan, "In Situ Passive Sampling of Sediment Porewater Enhanced by Periodic Vibration," Environ. Sci. Technol., 2016, pp. 8741-8749, vol. 50.
SiREM—Introducing SiREM's New Quarterly Newsletter; http://www.siremlab.com/introducing-sirems-new-quarterly-newsletter/ ; 2018.

* cited by examiner

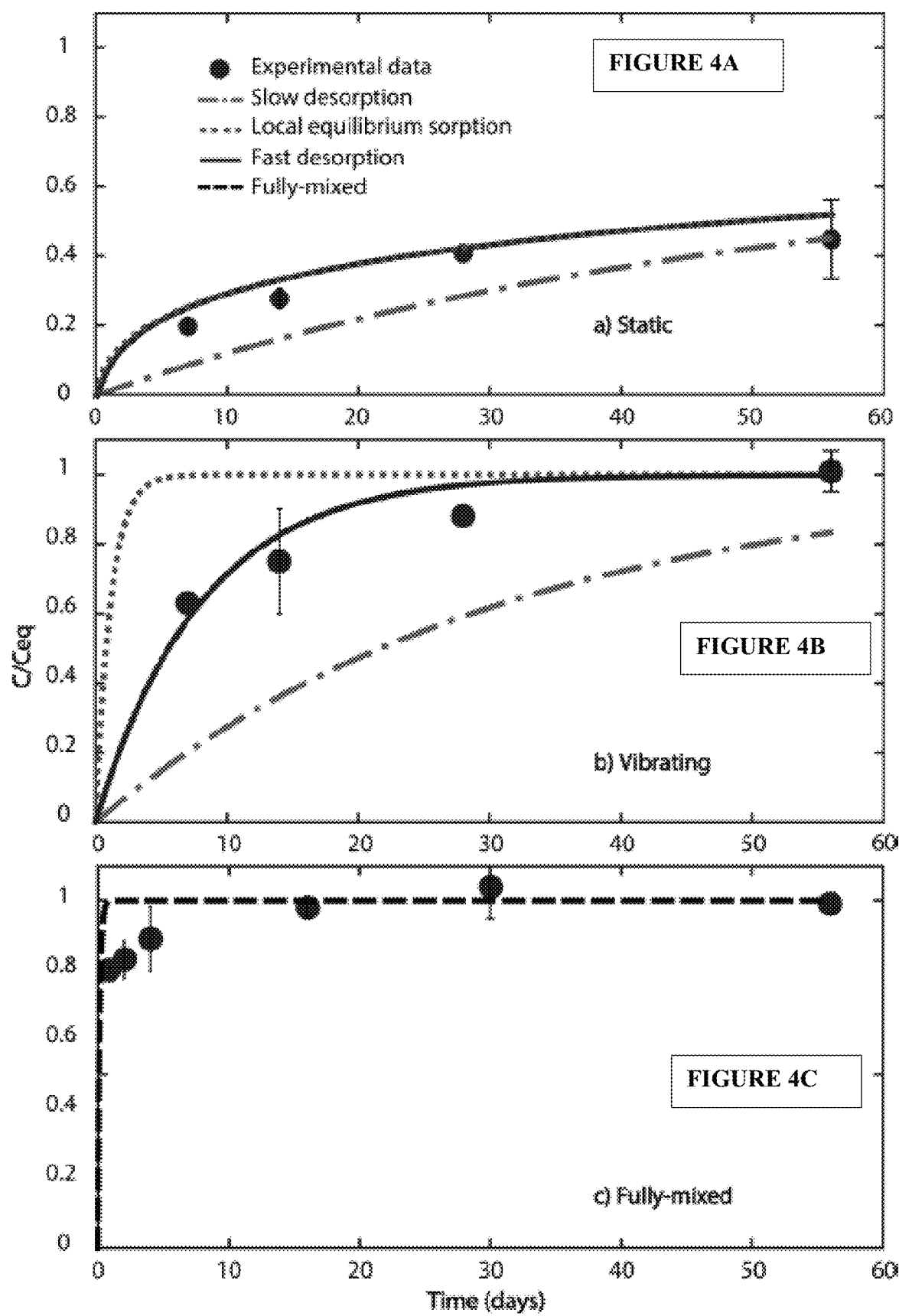

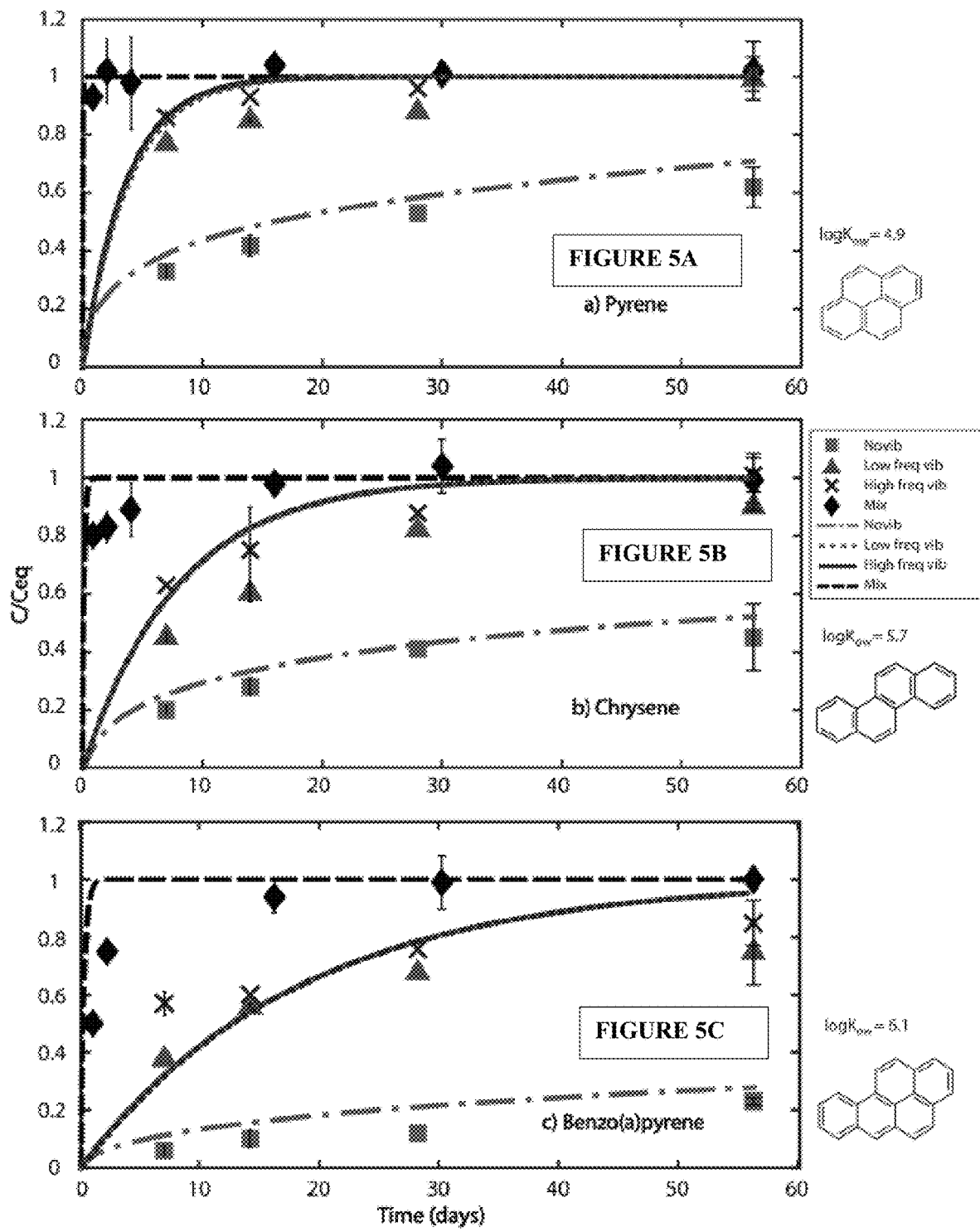

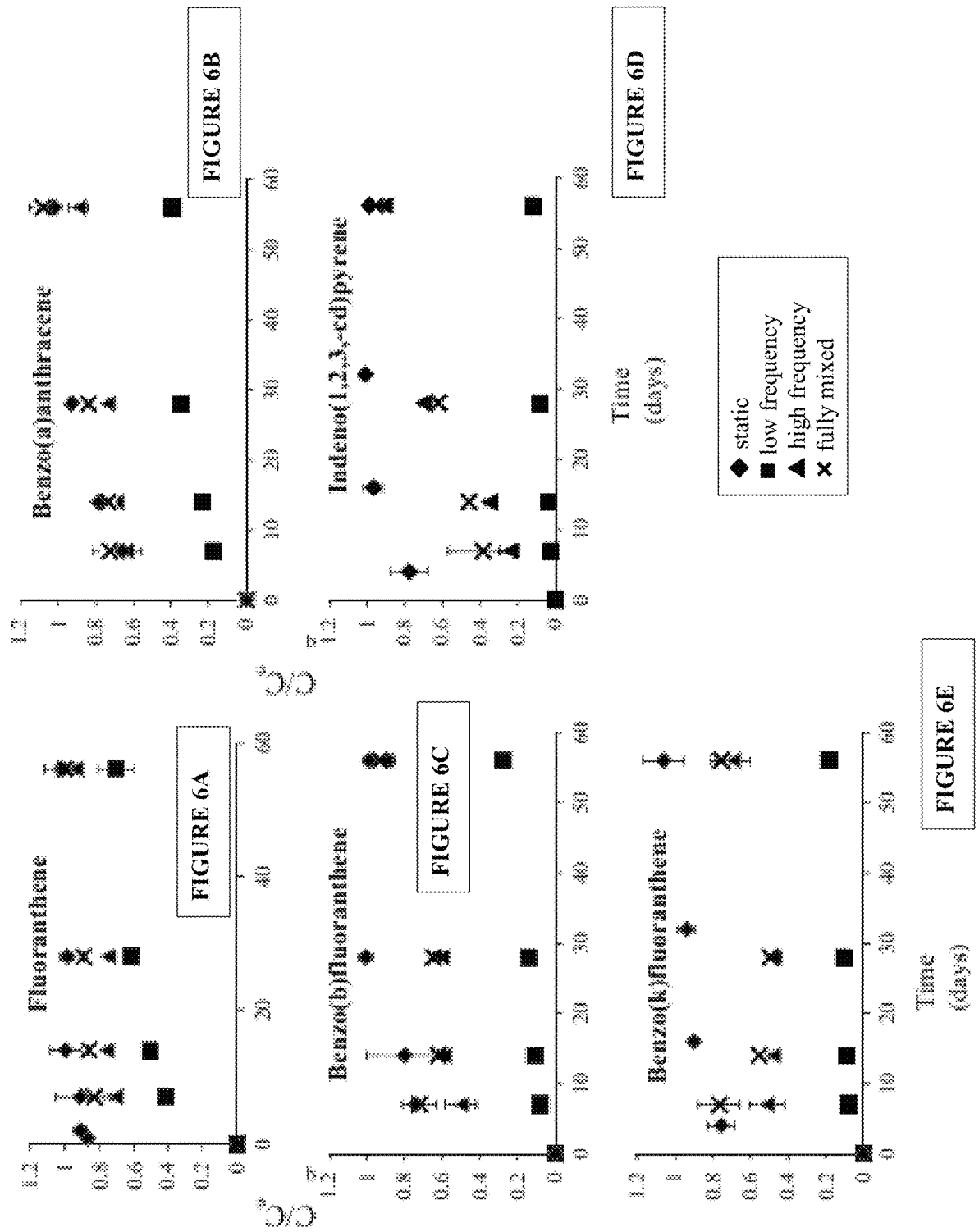

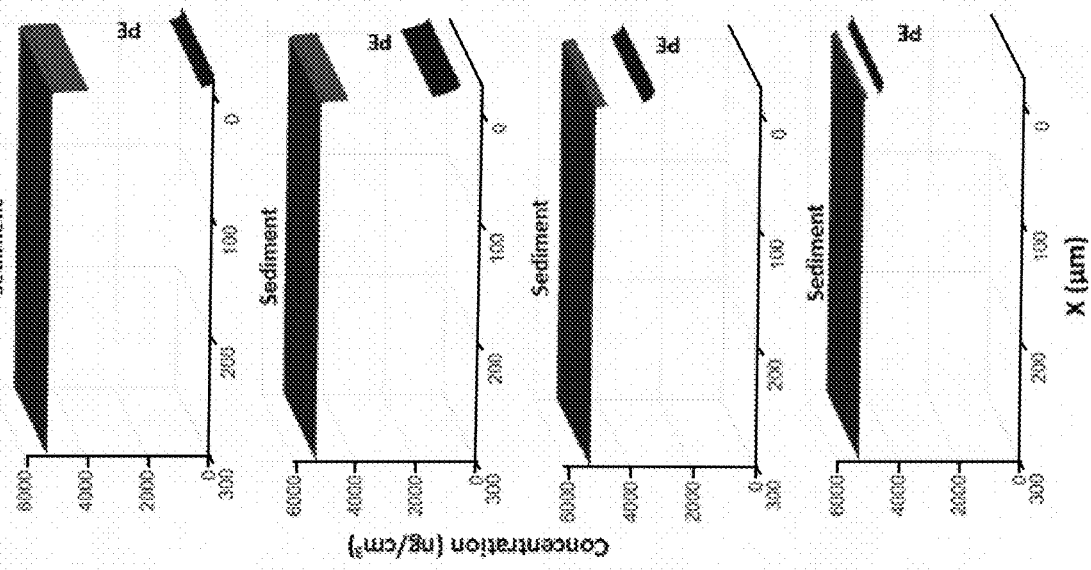
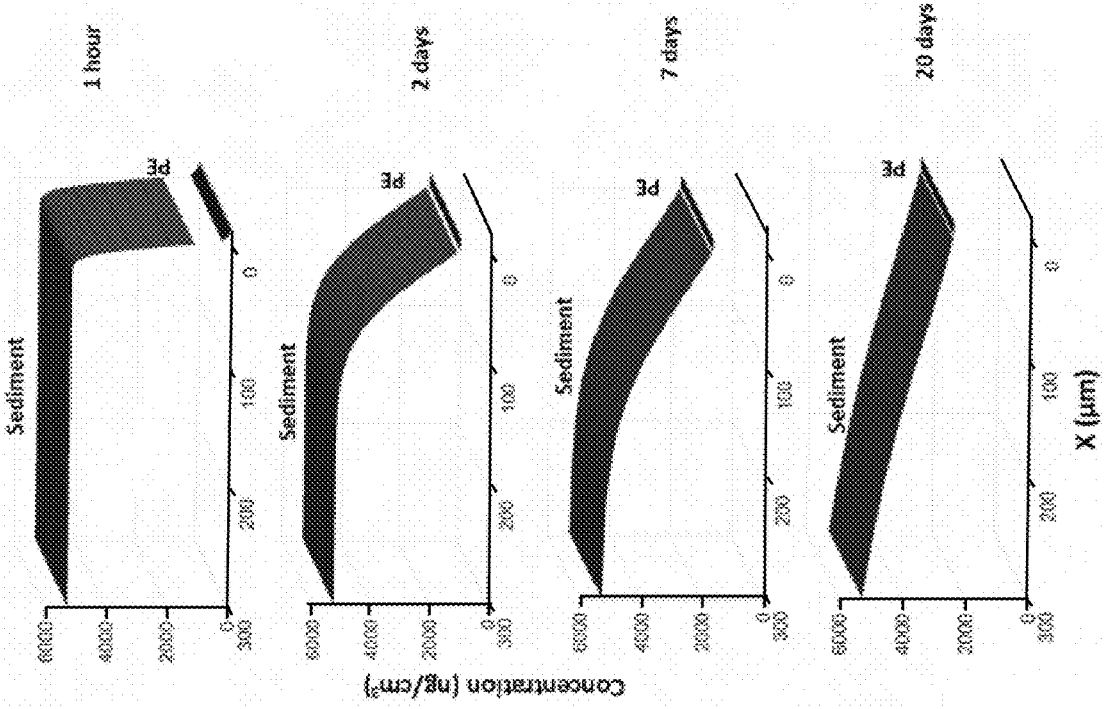
FIGURE 10A
FIGURE 10B

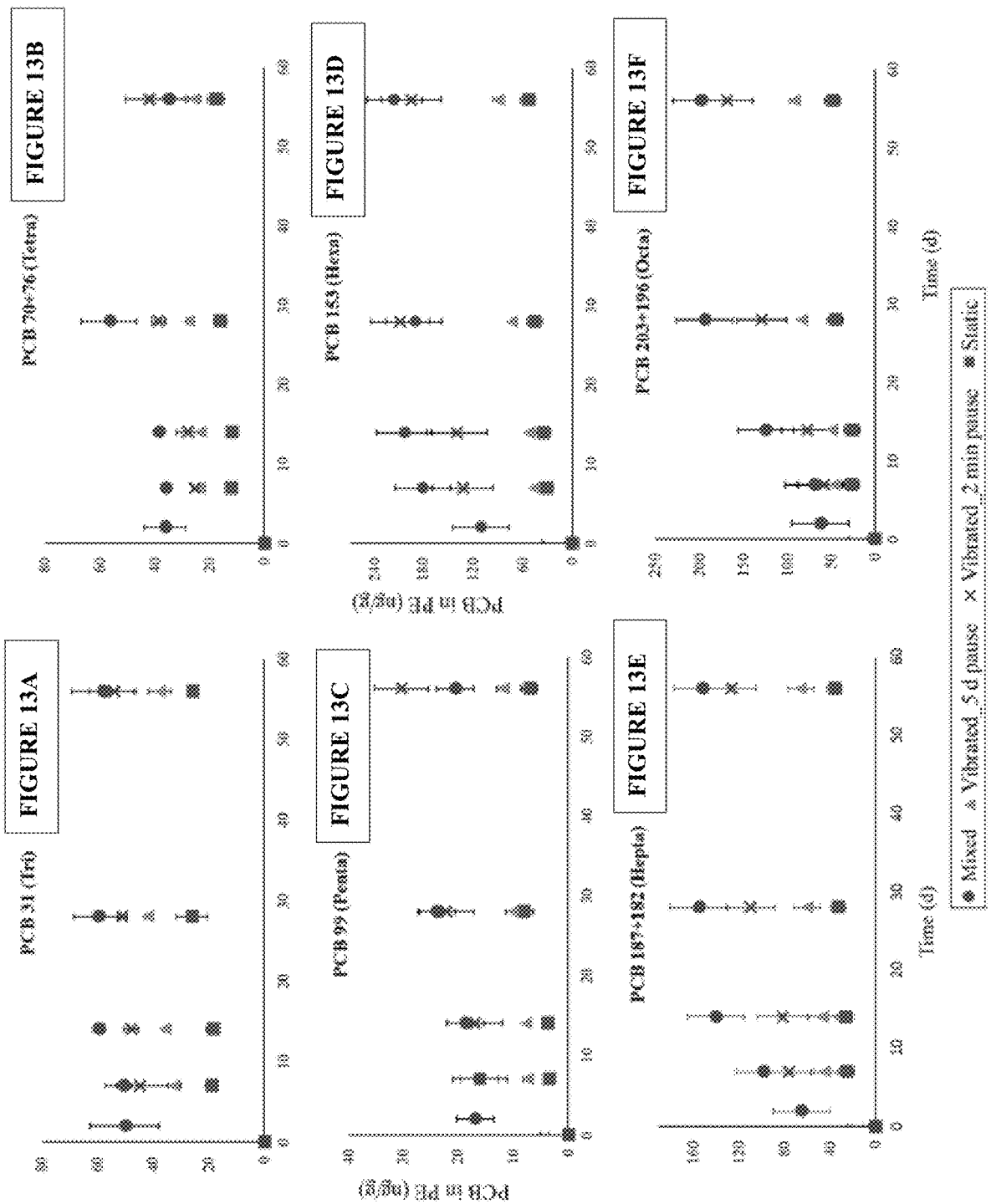

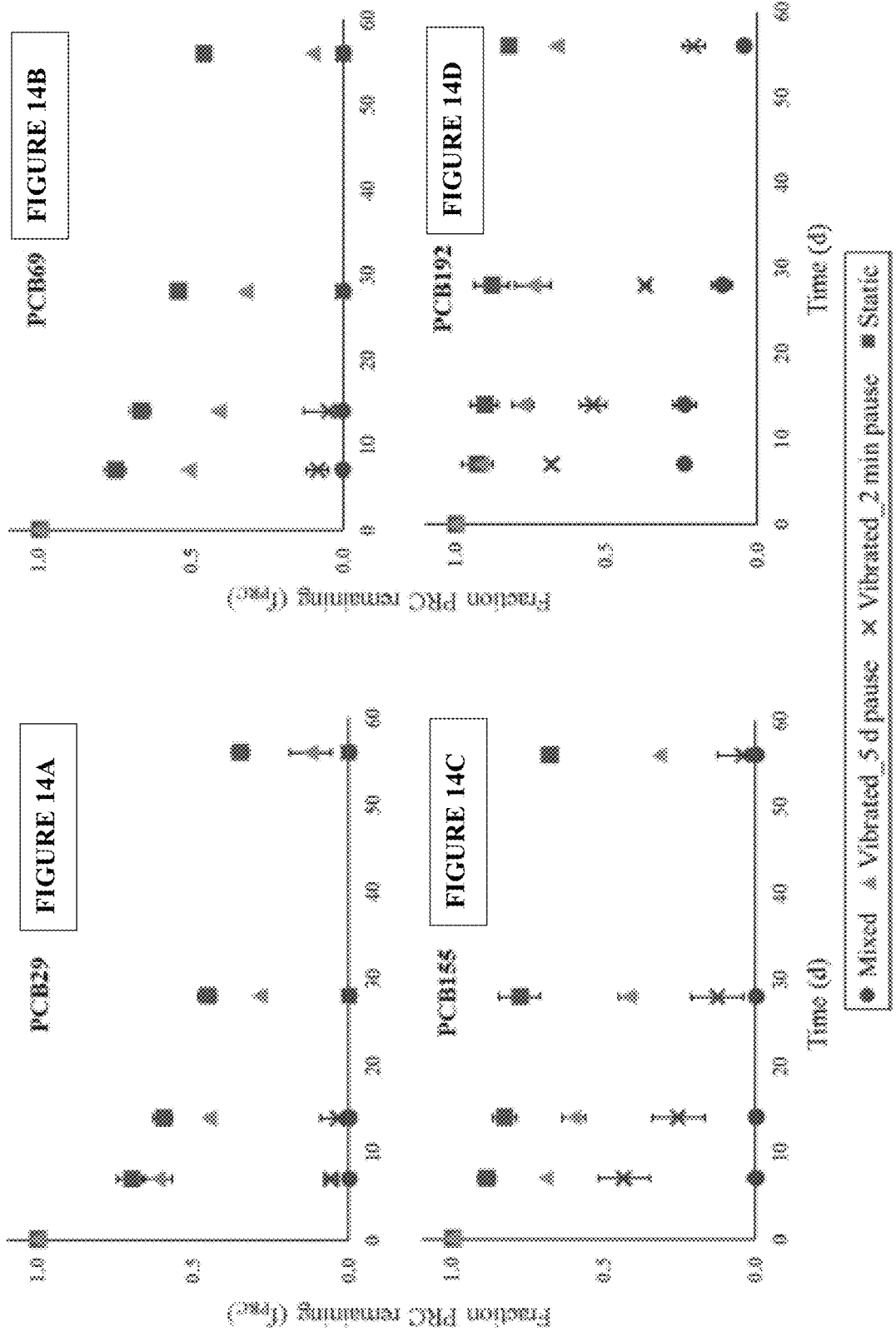

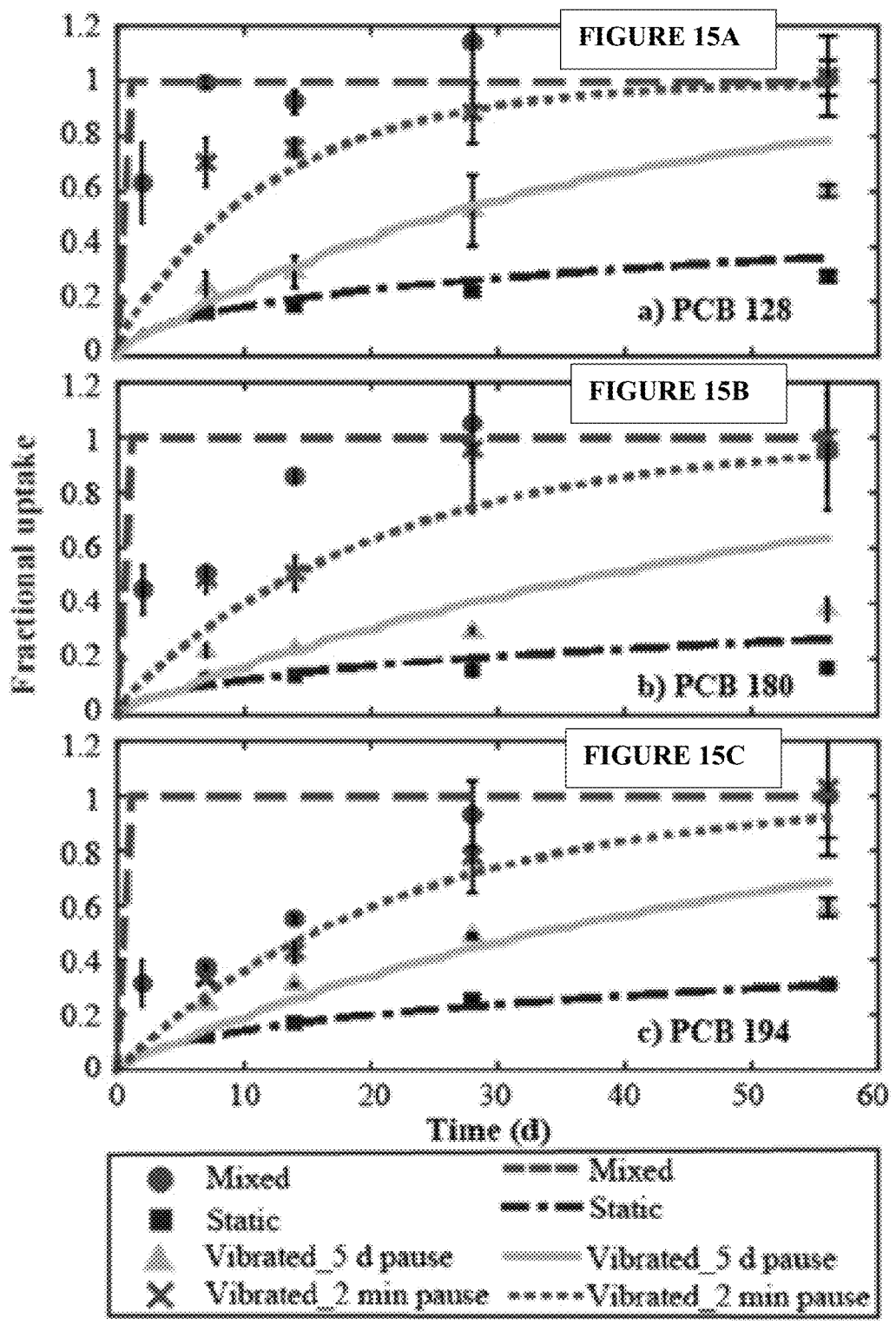

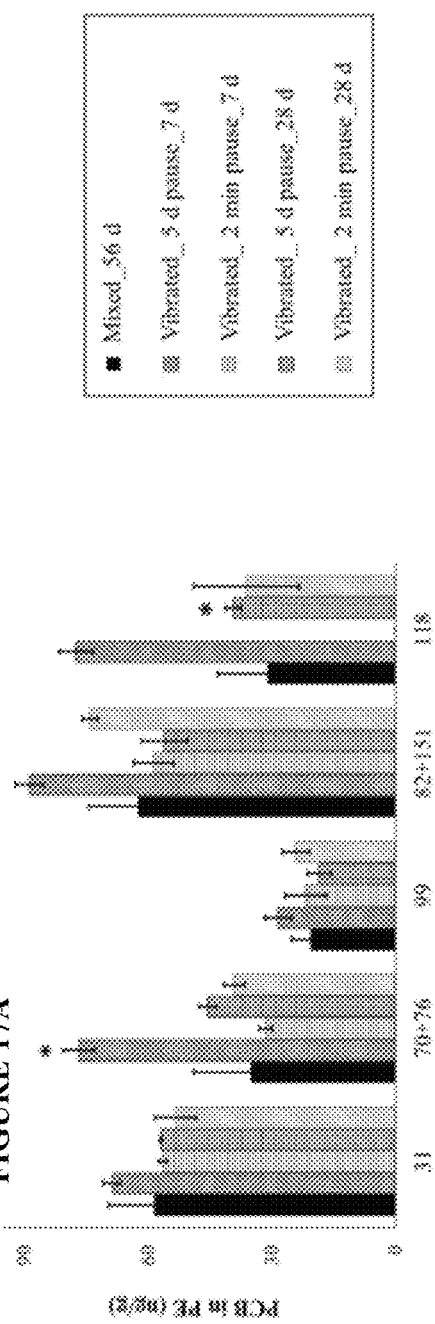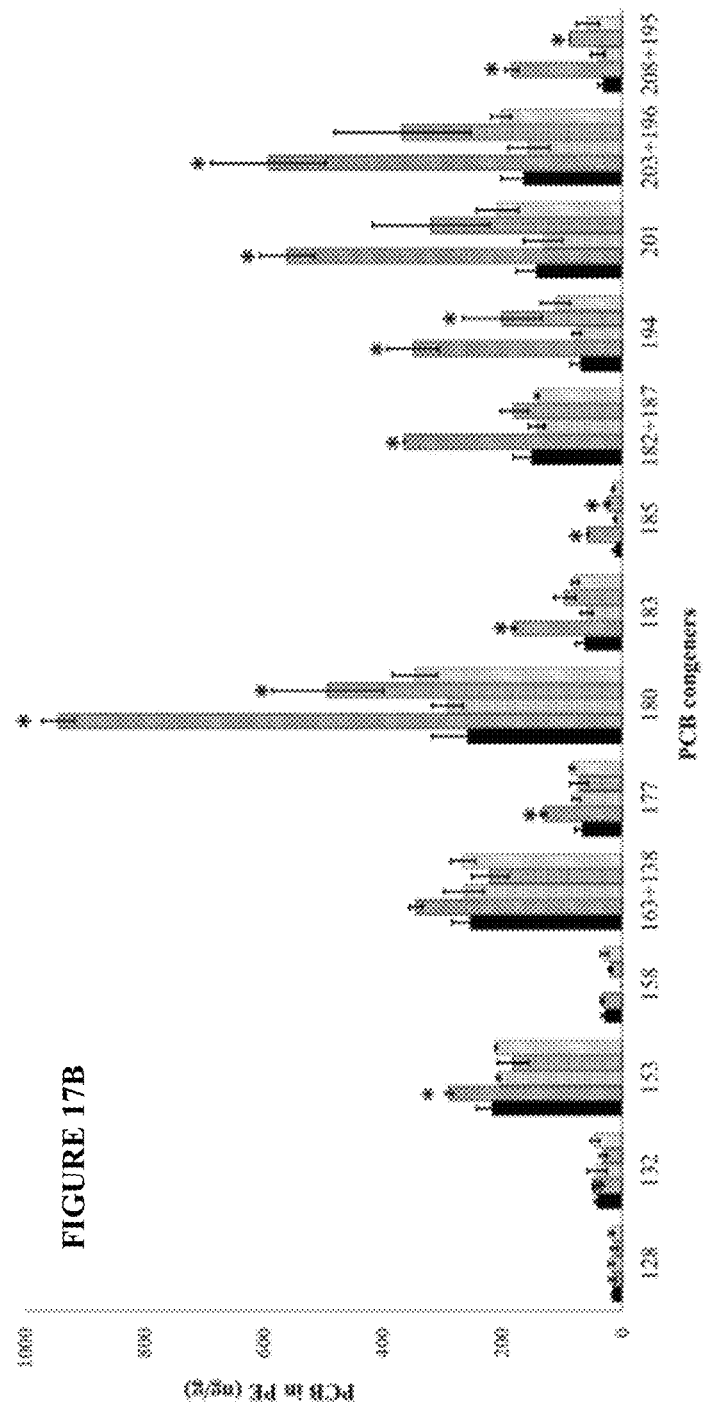
FIGURE 17A
FIGURE 17B

ACTIVELY SHAKEN IN-SITU PASSIVE SAMPLING DEVICE

CROSS REFERENCE TO RELATED APPLICATIONS

This application is filed under the provisions of 35 U.S.C. § 111(a) and claims priority to U.S. Provisional Patent Application No. 62/401,366 filed on Sep. 29, 2016 in the name of Upal Ghosh and entitled "Actively Shaken In-Situ Passive Sampler to Measure Freely Dissolved Pollutant Concentration in Sediment Porewater," which is hereby incorporated by reference herein in its entirety.

STATEMENT REGARDING FEDERALLY SPONSORED RESEARCH

Portions of this invention may have been financially supported by the United States Government support under a grant from the U.S. Department of Defense Strategic Environmental Research and Development Program under Project Number ER-2540. (contract # W912HQ-14-P-0111)

FIELD

The present invention relates to the field of analyzing the environment, e.g., surface water, aquatic sediment, and soil, to determine the concentration of an analyte using a passive sampling device.

BACKGROUND OF THE INVENTION

Freely dissolved concentration in sediment pore water is a critical measurement that is useful in assessing fate, transport, and bioavailability of hydrophobic pollutants in sediment (Mayer, 2014). Accurate measurement of low aqueous concentrations of hydrophobic compounds is challenging due to the association with colloidal and dissolved organic matter in pore water which has led to the development of passive sampling approaches using well characterized polymeric materials. When the polymeric material is able to reach equilibrium with the sediment pore water, such as in a well-stirred laboratory measurement, the estimation of freely dissolved pore water concentration ($C_{free}$) becomes a trivial exercise based on the known partition constant of the polymeric medium (Mayer, 2003; Ghosh, 2014). However, in several situations, an in-situ measurement in sediment is desired, and such measurements have been challenged by the difficulty in reaching equilibrium between pore water and the polymer as mass transfer through the static depletion layer outside the polymer becomes limiting in the absence of active mixing (Lampert, 2010). It has been shown that for strongly hydrophobic compounds equilibrium may not be achieved in the field even after one year (Lohmann, 2011). Several researchers have adopted the use of performance reference compounds (PRCs) dosed in the polymer to assess the kinetics of mass transfer and correct for non-equilibrium (Huckins, 2006; Huckins, 2002; Fernandez, 2009; Booij, 2010; Booij, 2003; Fernandez, 2014; Oen, 2011; Tomaszewski, 2008; Apell, 2014). While corrections based on PRC loss work reasonably well for compounds with low to midrange hydrophobicity, the corrections become increasingly erroneous for strongly hydrophobic compounds when the departure from equilibrium increases (Apell, 2014). Several approaches for calibration using PRC data have been suggested (Huckins, 2006; Huckins, 2002; Fernandez, 2009; Booij, 2010; Booij, 2003). In all of these approaches, the uncertainties introduced by the PRC correction are larger when the extent of equilibrium is low, which is the case for strongly hydrophobic compounds in the field.

A primary uncertainty in the PRC correction arises from the fact that nearly always it is the sediment side mass transfer in the immediate vicinity of the passive sampler that controls kinetics and as such, is dependent on the site-specific sorption characteristics of the sediment which can vary across orders of magnitude. For example Hawthorne (Hawthorne, 2006) reported a 3-4 orders of magnitude range for site-specific $K_{ocS}$. Thus, to be able to correct for non-equilibrium and estimate in-situ pore water concentrations we need to first have an estimate of site-specific partitioning of the analytes of interest. The loss of a few PRC compounds and adsorption into the sediment matrix then have to be used to infer the desorption behavior of a large range of analyte compounds from sediment (Fernandez, 2009).

Thinner polymeric materials can be used to increase the surface area to volume ratio and reduce the depletion per unit area. However, even with some of the thinnest polymers practically deployable in the field (e.g., 25 µm thick polyethylene), sediment-side mass transfer limitation can be significant. Making the polymers too thin makes them prone to damage during deployment in sediment, reduces the total mass of polymer sampling material (impacting detection limits), and also poses a physical challenge of insertion in sediments if the area is very large.

To address these challenges, the present inventors manipulated the external depletion layer in the sediment side of a passive sampler deployment, which overcomes the slow approach to equilibrium for hydrophobic organic compounds in static sediments. Specifically, the present invention relates to an apparatus and method to mechanically disrupt the static depletion layer outside the polymer surface using periodic vibration performed in-situ. Using the apparatus and method to mechanically disrupt the static depletion layer using periodic vibration, the present invention further relates to a method of determining the freely dissolved concentration of analyte in the porewater of sediment.

SUMMARY OF THE INVENTION

In a first aspect, a passive sampling device (PSD) is described, said PSD comprising at least one cage and at least one vibrating device, wherein at least one passive sampler is in each cage.

In a second aspect, a method of determining the amount of an analyte in an environment is described, said method comprising:
(a) positioning a PSD in the environment for time x, wherein the PSD comprises at least one cage and at least one vibrating device, wherein at least one passive sampler is in each cage;
(b) removing the PSD from the environment at the end of time x and removing the passive sampler material(s) from the cage(s);
(c) extracting the analyte from the passive sampler material using at least one extraction solvent; and
(d) calculating the amount of analyte collected in the PSD and optionally, making corrections for non-equilibrium.

In a third aspect, a method of determining the amount of an analyte in an environment is described, said method comprising:

(a) positioning a PSD in the environment for time x, wherein the PSD comprises at least one cage and at least one vibrating device, wherein at least one passive sampler is in each cage;
(b) vibrating the PSD during time x for at least one time y;
(c) removing the PSD from the environment at the end of time x and removing the passive sampler material(s) from the cage(s);
(d) extracting the analyte from the passive sampler material using at least one extraction solvent; and
(e) calculating the amount of analyte collected in the PSD and optionally, making corrections for non-equilibrium.

In another aspect, a method of determining the amount of an analyte in an environment is described, said method comprising:
(a) positioning a PSD in the environment for time x, wherein the PSD comprises at least one cage and at least one vibrating device, wherein at least one passive sampler is in each cage;
(b) vibrating the PSD during time x for at least one time y;
(c) pausing the vibrations of the PSD for at least a time z;
(d) optionally repeating (b) and (c) in a range from at least 1 to at least 1000 times during time x;
(e) removing the PSD from the environment at the end of time x and removing the passive sampler material(s) from the cage(s);
(f) extracting the analyte from the passive sampler material using at least one extraction solvent; and
(g) calculating the amount of analyte collected in the PSD and optionally, making corrections for non-equilibrium.

Other aspects, features and embodiments of the invention will be more fully apparent from the ensuing disclosure and appended claims.

BRIEF DESCRIPTION OF THE FIGURES

FIG. 4A is a fractional uptake of chrysene in PE passive sampler in a static system. Experimental data are shown by circles and model simulations are shown by lines.

FIG. 4B is a fractional uptake of chrysene in PE passive sampler in a vibrating system. Experimental data are shown by circles and model simulations are shown by lines.

FIG. 4C is a fractional uptake of chrysene in PE passive sampler in a fully-mixed system. Experimental data are shown by circles and model simulations are shown by lines.

FIG. 5A is a fractional uptake of pyrene in PE passive sampler in a static, low frequency vibration, high-frequency vibration, and fully-mixed system. Experimental data are shown by symbols and fast desorption model simulations are shown by lines.

FIG. 5B is a fractional uptake of chrysene in PE passive sampler in a static, low frequency vibration, high-frequency vibration, and fully-mixed system. Experimental data are shown by symbols and fast desorption model simulations are shown by lines.

FIG. 5C is a fractional uptake of benzo(a)pyrene in PE passive sampler in a static, low frequency vibration, high-frequency vibration, and fully-mixed system. Experimental data are shown by symbols and fast desorption model simulations are shown by lines.

FIG. 6A is a fractional uptake of fluoranthene in PE passive sampler in a static, low frequency vibration, high-frequency vibration, and fully-mixed system.

FIG. 6B is a fractional utake of benzo(a)anthracene in PE passive sampler in a static, low frequency vibration, high-frequency vibration, and fully-mixed system.

FIG. 6C is a fractional uptake of benzo(b)fluoranthene in PE passive sampler in a static, low frequency vibration, high-frequency vibration, and fully-mixed system.

FIG. 6D is a fractional uptake of indeno(1,2,3-cd)pyrene in PE passive sampler in a static, low frequency vibration, high-frequency vibration, and fully-mixed system.

FIG. 6E is a fractional uptake of benzo(k)fluoranthene in PE passive sampler in a static, low frequency vibration, high-frequency vibration, and fully-mixed system.

FIG. 10A is a model simulation of chrysene concentration profile within sediment and PE for static vibration deployments.

FIG. 10B is a model simulation of chrysene concentration profile within sediment and PE for periodic vibration deployments.

FIG. 13A is a comparison of uptake profile of PCB 31 (Tri) into PE in static, vibrated, and mixed systems. Error bars represent the mean±one standard deviation (n=3).

FIG. 13B is a comparison of uptake profile of PCB 70+16 (Tetra) into PE in static, vibrated, and mixed systems. Error bars represent the mean±one standard deviation (n=3).

FIG. 13C is a comparison of uptake profile of PCB 99 (Penta) into PE in static, vibrated, and mixed systems. Error bars represent the mean±one standard deviation (n=3).

FIG. 13D is a comparison of uptake profile of PCB 153 (Hexa) into PE in static, vibrated, and mixed systems. Error bars represent the mean±one standard deviation (n=3).

FIG. 13E is a comparison of uptake profile of PCB 187+182 (Hepta) into PE in static, vibrated, and mixed systems. Error bars represent the mean±one standard deviation (n=3).

FIG. 13F is a comparison of uptake profile of PCB 203+196 (Octa) into PE in static, vibrated, and mixed systems. Error bars represent the mean±one standard deviation (n=3).

FIG. 14A is a comparison of remaining PCB29 fraction in PE in static, vibrated, and mixed systems. Error bars represent the mean±one standard deviation (n=3).

FIG. 14B is a comparison of remaining PCB69 fraction in PE in static, vibrated, and mixed systems. Error bars represent the mean±one standard deviation (n=3).

FIG. 14C is a comparison of remaining PCB155 fraction in PE in static, vibrated, and mixed systems. Error bars represent the mean±one standard deviation (n=3).

FIG. 14D is a comparison of remaining PCB192 fraction in PE in static, vibrated, and mixed systems. Error bars represent the mean±one standard deviation (n=3).

FIG. 15A is a fractional uptake of PCB 128 in PE passive samplers in four differently exposed systems. Experimental data are shown by symbols, and fast desorption model simulations are shown by lines. Error bars represent the mean±one standard deviation (n=3).

FIG. 15B is a fractional uptake of PCB 180 in PE passive samplers in four differently exposed systems. Experimental data are shown by symbols, and fast desorption model simulations are shown by lines. Error bars represent the mean±one standard deviation (n=3).

FIG. 15C is a fractional uptake of PCB 194 in PE passive samplers in four differently exposed systems. Experimental data are shown by symbols, and fast desorption model simulations are shown by lines. Error bars represent the mean±one standard deviation (n=3).

FIG. 17A is a comparison of 56-day mixed equilibrium concentration in PE with PRC-corrected PE equilibrium concentration measured using 7-day and 28-day vibrated passive samplers. The PCB congeners belong to pentachloro- and lower molecular weight congeners. The corrected concentrations that are statistically different from the 56-day mixed equilibrium concentrations values (with alpha level of 5%) are indicated with an asterisk. Error bars represent the mean±one standard deviation (n=3).

FIG. 17B is a comparison of 56-day mixed equilibrium concentration in PE with PRC-corrected PE equilibrium concentration measured using 7-day and 28-day vibrated passive samplers. The PCB congeners belong to hexachloro- and higher molecular weight congeners. The corrected concentrations that are statistically different from the 56-day mixed equilibrium concentrations values (with alpha level of 5%) are indicated with an asterisk. Error bars represent the mean±one standard deviation (n=3).

DETAILED DESCRIPTION, AND PREFERRED EMBODIMENTS THEREOF

Figure 1:
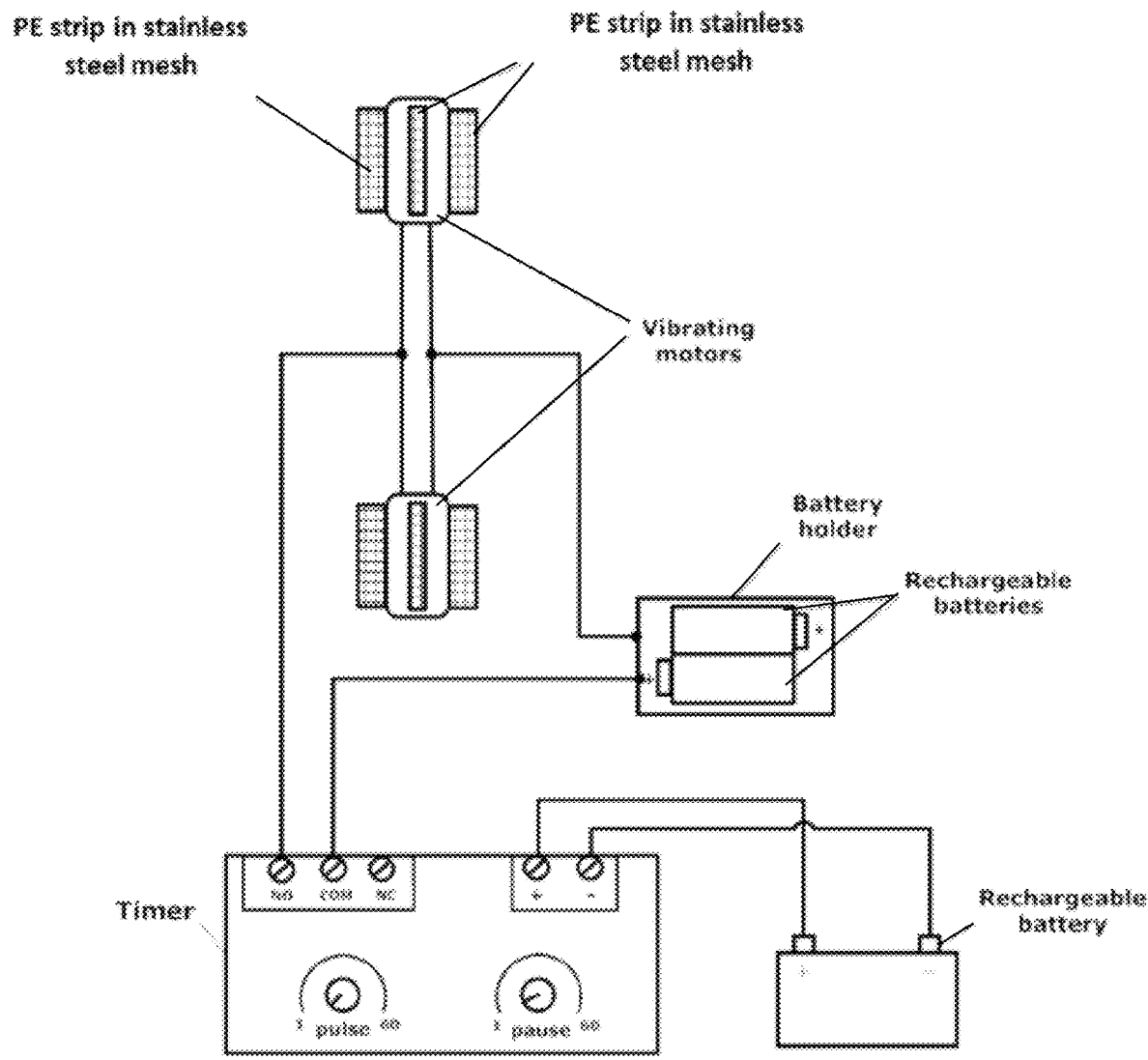
FIG. 1 illustrates a wire diagram of an embodiment of the vibrating passive sampler described herein.

The present invention relates to an apparatus and method providing the periodic vibration of passive sampler devices during exposure to an environment to enhance the mass transfer of analytes, e.g., polycyclic aromatic hydrocarbons (PAHs) and polychlorinated biphenyls (PCBs), from the environment into the passive sampler.

While passive sampling has emerged as an innovative way to accurately measure freely dissolved concentrations of hydrophobic organics in water, measurements in sediment pore water has been challenged by the slow approach to equilibrium, especially for strongly hydrophobic compounds. A recent review article on passive sampling by Booij (Booij, 2015) concluded that options to reduce time for equilibrium are limited to manipulation of area/volume ratio, choice of sampler material, and flow rate. Past work has led to significant optimization of the physical aspects of the passive samplers, yet attainment of equilibrium remains elusive for strongly hydrophobic compounds especially for in-situ sediment porewater measurements. Also, there is little that can be done in the sediment environment to enhance porewater flow rate.

One particularly challenging issue historically with passive sampling devices (PSDs) is that the time period required for the concentrations of compounds to reach steady state can be several weeks or months (Ghosh, 2014) under most conditions in the environmental media in which PSDs are deployed. These long time periods are often not practical for several reasons, especially the increasing likelihood of loss and/or physical alteration of samplers due to theft, vandalism or other natural factors (e.g., water currents, sediment burial, organism growth), and the cost associated with multiple mobilizations of equipment and crew to the field for deployment and retrieval.

The present invention advances the practice of passive sampling by addressing a key bottleneck through the introduction of periodic vibration in the sampling platform. Although not wishing to be bound by theory, it is thought that the periodic vibration disrupts the static depletion layer that develops in the sediment side and slows mass transfer. While PRC corrections have allowed extension of passive sampling to compounds that do not achieve equilibrium during a reasonable period of deployment, the introduction of vibration greatly enhances approach to equilibrium, reduces deployment times, and extends the use of passive sampling to strongly hydrophobic compounds.

By a "passive sampling device" or "PSD" or simply a "passive sampler" is meant a device that allows passive sampling of compounds from the environment, including compounds of interest, by passive diffusion. In other words, a PSD absorbs compounds that are in the environment into which the PSD is placed. Passive diffusion occurs when compounds move from an area of high concentration to an area of lower concentration until equilibrium conditions are reached.

A PSD, in some embodiments, absorbs only compounds that are mobile and bioavailable in the environment into which the PSD is placed. A PSD does not actively sample the environment but rather passively absorbs compounds that are present in the environment. Thus, a PSD can comprise any type of material that is able to absorb compounds. Such materials include, without limitation, silicone rubber, low-density polyethylene (LDPE), polyethylene (PE), polyoxymethylene (POM), polydimethylsiloxane (PDMS), polyethersulfone (PES), and polyacrylate (PA). For example, LDPE is non-porous, so it is selective and only absorbs fully dissolved and unbound molecules (e.g., free analyte).

While a PSD will absorb compounds from the environment, typically a particular analyte of interest is sought to be detected and measured. An "analyte of interest" (or simply "analyte") is any molecule or chemical that a PSD is particularly seeking out when using a PSD to analyze an environment. In some embodiments, the analyte is a hydrophilic organic chemical. In some embodiments, the analyte is a hydrophobic organic chemical. Because the analyte of interest is often known in advance of placing a PSD in an environment, the material used to make the PSD can be chosen that will easily absorb the analyte of interest, as readily understood by the person skilled in the art. Analytes include, but are not limited to, polycyclic aromatic hydrocarbon (PAH), polychlorinated biphenyls (PCB), dichlorodiphenyltrichloroethane, polybrominated diphenyl ethers (PBDE), triclosan, or polychlorinated dibenzo-p-dioxins/dibenzofurans.

By "performance reference compound" or "PRC" is meant a chemical that is added to the PSD before placement of the PSD in the environment to be analyzed. For example, the PRC may be embedded into and/or adsorbed on the passive sampler prior to placing the passive sampler into the environment.

As used herein, by "environment" is meant any type of environment that is desired to be analyzed. An environment thus is any environment into which a PSD can be placed and includes, without limitation, liquid (e.g., water), gas (e.g., air), and solid environments. Thus, environments and "environmental samples" within this disclosure include, without limitation, biological fluids (e.g., blood or urine), water (e.g., surface water or water deep in a sea, ocean, river, stream, pond, or lake), aquatic sediment (e.g., the bottom of a pond or on the beach of an ocean), soil (e.g., garden soil or soil near an industrial site), and sludge. The environment can be at any temperature. For example, the environment may be very cold (e.g., −80° C. or −20° C.), may be at or just below freezing (e.g., if the environment includes snow or ice), may be at room temperature, at 37° C. (e.g., if the environment is inside a living organism such as inside a human body), or may be at a very high temperature (e.g., over 60° C. or over 100° C.).

Passive sampling devices are well known in the art, with and without the use of a PRC. See, for example, US Patent Publication No. US20140069184, U.S. Pat. No. 7,059,206, PCT Patent Publication No. WO2012071629, US Patent Publication No. US20140041446, US Patent Publication No. US20110070597, Huckins, 2002; Apell, 2014; Ghosh, 2014, all of which are incorporated herein by reference in their entireties.

In the first aspect, a passive sampling device (PSD) is described, said PSD comprising a vibration device, wherein the vibration device periodically disrupts the depletion layer in a passive sampler deployed in an environment, e.g., sediment. In one embodiment, the PSD comprises at least one cage and at least one vibrating device, wherein at least one passive sampler is in each cage. In another embodiment, the PSD comprises at least one cage and at least one vibrating device, wherein at least one passive sampler is in each cage, and wherein the at least one cage is in direct contact with the at least one vibrating device. In still another embodiment, the PSD comprises at least one cage, at least one vibrating device, and at least one pulse-pause timer, wherein at least one passive sampler is in each cage. In yet another embodiment, the PSD comprises at least one cage, at least one vibrating device, and at least one pulse-pause timer, wherein at least one passive sampler is in each cage, and wherein the at least one cage is in direct contact with the at least one vibrating device.

Figure 2A:
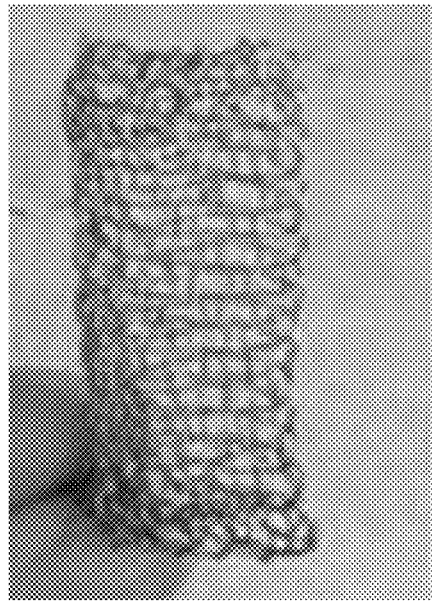
FIG. 2A is a photograph of a polymer strip enclosed in a metal cage.

The at least one passive sampler comprises materials selected from the group consisting of silicone rubber, low-density polyethylene (LDPE), polyethylene (PE), polyoxymethylene (POM), polydimethylsiloxane (PDMS), polyethersulfone (PES), and polyacrylate (PA), preferably polyethylene (PE). In one embodiment, the passive sampler material is substantially devoid of to residual monomers and any target and non-target contaminants, which can be achieved by pre-cleaning the passive sampler material with a pre-cleaning solvent such as hexane, acetone, methanol, acetonitrile, or any combination thereof As defined herein, a "cage" or "mesh" corresponds to a structure that the passive sampler material can be inserted into. For example, the cage can have a pocket which the passive sampler can be sandwiched within. The structure can comprise metal, polymer, or a combination thereof, so long as the structure is substantially resistant to corrosion in, and is durable enough to be placed in, the environment to be tested. For example, the cage or mesh can comprise copper, stainless steel and alloys comprising copper, nickel, and/or chromium. The cage or mesh should be robust enough to contain the passive sampler material but open to the environment for the flow of analyte into and out of the cage or mesh. Embodiments of the cage are shown in FIG. 2A, although these embodiments are not intended to limit the cage in any way. Alternatives shapes and sizes can be readily envisioned by the person skilled in the art, with the only limitation being the attachment of at least one cage to the motor. The cage can also include structural supports to ensure they are not readily damaged in the environment.

Vibrating devices are known in the art and can include motors powered using AC or DC, depending on the environment being tested. Alternatively, the device can be made to vibrate in the field using a spring loaded device or by utilizing natural forces such as tidal energy, water flow, or solar energy. The devices can have range of vibration speeds. The vibrating devices are preferably substantially resistant to corrosion in, and durable enough to be placed in, the environment of to be tested.

For example, small vibration motors used in haptic feedback in cell phones and other electronic devices create vibration in in-situ passive sampling frames programmed to trigger at pre-determined time intervals.

Passive sampling devices can vary greatly in size, shape, and material. Nearly all PSDs share the same core design characteristics. First, PSDs have a depletion layer between the sampled medium and the receiving phase. The diffusion across this depletion determines the rate at which the target analyte is sampled. When deployed, the target analyte accumulates in the sampler by diffusion through this static layer of water/sediment or by permeation through a membrane. Periodic vibrations, as described herein, should enhance the diffusion of the analyte through this static layer of water or sediment.

It is understood that the PSD of the first aspect may further comprise at least one of wires, circuit boards, cords, batteries, computers, microcontrollers, vibration sensors, and environment-resistant containers. Further, it is understood that the PSD may be further attached to a structure to ensure it remains in position for the length of the experiment. For example, the structure can be a stake or other structure that can be driven into a solid environment. The PSDs of the first aspect can be accessed remotely so the user can track and alter the parameters as needed.

In a second aspect, a method of determining the amount of an analyte in an environment is described, said method comprising:

(a) positioning a PSD of the first aspect in the environment for time x;

(b) removing the PSD from the environment at the end of time x and removing the passive sampler material(s) from the cage(s);

(c) extracting the analyte from the passive sampler material using at least one extraction solvent; and
(d) calculating the amount of analyte collected in the PSD and optionally, making corrections for non-equilibrium.

In one embodiment of the second aspect, a method of determining the amount of an analyte in an environment comprises:
(a) positioning a PSD of the first aspect in the environment for time x;
(b) vibrating the PSD of the first aspect during time x for at least one time y;
(c) removing the PSD from the environment at the end of time x and removing the passive sampler material(s) from the cage(s);
(d) extracting the analyte from the passive sampler material using at least one extraction solvent; and
(e) calculating the amount of analyte collected in the PSD and optionally, making corrections for non-equilibrium.

In another embodiment of the second aspect, a method of determining the amount of an analyte in an environment comprises:
(a) positioning a PSD of the first aspect in the environment for time x;
(b) vibrating the PSD of the first aspect for at least one time y;
(c) pausing the vibrations of the PSD of the first aspect for at least a time z;
(d) optionally repeating (b) and (c) in a range from at least 1 to at least 1000 times during time x;
(e) removing the PSD from the environment at the end of time x and removing the passive sampler material(s) from the cage(s);
(f) extracting the analyte from the passive sampler material using at least one extraction solvent; and
(g) calculating the amount of analyte collected in the PSD and optionally, making corrections for non-equilibrium.

In should be appreciated that the amount of an analyte in an environment calculated using any embodiment of the second aspect can be an equilibrium amount or less than an equilibrium amount, depending on parameters such as, but not limited to, times x, y, and/or z, the passive sampler material, the analyte, and the environment. In a preferred embodiment, the experimental parameters permitted the determination of the equilibrium amount of analyte ($C_{PSM,Eq}$), wherein PSM is the passive sampler material used.

After exposure to the environment, a PSD is weighed and extracted with a solvent. The particular solvent used will depend upon the type material of the PSD and/or the type of analysis used to analyze the extract (i.e., possibly containing the analyte). The type of material of the PSD, in turn, can be selected based on the type of analytes sought to be measured.

For example, if the analyte is a polycyclic aromatic hydrocarbon (PAH) or a polychlorinated biphenyl (PCB), one non-limiting passive sampler material that may be used in a PSD is polyoxymethylene (POM). Non-limiting solvents useful for extraction from POM include hexane, methanol, acetone, or acetonitrile, or any combination of the foregoing. Another analyte that can be analyzed with a PSD composed of POM is oil. Solvents useful for extraction of oil from POM include hexane and/or acetone.

Likewise, if an analyte is a PCB, a PAH, dichlorodiphenyltrichloroethane, a polybrominated diphenyl ether (PBDE), or triclosan, one non-limiting passive sampler material that may be used in a PSD is polyethylene (PE). Solvents useful for extraction from PE include hexane, methanol, acetonitrile, or any combination or two or more of the foregoing.

The time x is readily determinable by the person skilled in the art depending on what analyte is being sampled, what passive sampler material is being used, how long it takes to reach equilibrium of analyte absorption/adsorption to the passive sampler material, the parameters for time y and z chosen, and how long is provided for the experiment. Preferably, the time x is at least 7 days.

The time of vibration y may vary, but can be in a range from about 1 sec to about 60 seconds, preferably about 1 seconds to about 10 seconds, and most preferably about 2 seconds to about 8 seconds. It was surprisingly discovered that longer vibration periods did not enhance the extent of analyte collection. Further, longer vibration periods require more power and can possibly damage the PSD. Accordingly, a short pulse, on the order of about 2 seconds to about 6 seconds, is preferred.

The time of pausing z between pulses y, may also vary, but can be in a range from about 1 minute to about 1 day, preferably about 2 minutes to about 10 minutes, as will be discussed in the experimental section. Shorter pause periods require more power and can possibly lead to earlier damage of the PSD. Accordingly, a longer pause between pulses, on the order of about 5 minutes, 30 minutes, 1 hour, 5 hours, 10 hours, or about 1 day, are preferred.

It should be appreciated that the pulse-pause process of steps (b) and (c) can be carried out just once or can be repeated many times, e.g., in a range from 1 to 1000 times, during time x. Further, the length of each pulse can be the same as or different from one another. Also, the length of each pause can be the same as or different from one another. In one embodiment, each pulse occurs for the same length of time y. In another embodiment, each pause occurs for the same length of time z. In still another embodiment, each pulse occurs for the same length of time y and each pause occurs for the same length of time z.

In a third aspect, a method of determining the freely dissolved pore water concentrations ($C_{w0}$) of an analyte in an environment is described, said method comprising:
(a) determining the equilibrium concentration of analyte in the passive sampler material(s) ($C_{PSM,Eq}$), using the method of the second aspect; and
(b) calculating the freely dissolved pore water concentrations ($C_{w0}$) of the analyte using:

$$C_{w0} = \frac{C_{PSM,Eq}}{K_{PSMw}}$$

wherein $K_{PSMw}$ is PSM-water partition coefficient (cm$^3$/cm$^3$). An example of this equation using PE as the passive sampler material is shown in Example 1.

In a fourth aspect, a PRC is added to the passive sampler material of the PSD of the first aspect (and hence the methods of the second and third aspect) to reduce the time period needed for the PSD to be present in the environment in which the PSD is placed.

A traditional PRC may include stable isotope-labeled or deuterated forms of the analyte of interest (i.e., an analyte that will be diffusing into the environment being analyzed). For example, PRCs can include deuterated phenanthrene and deuterated pyrene. Measuring a traditional PRC requires analysis on a high performance liquid chromatography (HPLC) instrument or a gas chromatograph. As introduced hereinabove, the use of one or more PRCs can enable the estimation of equilibrium of analytes in PSDs exposed to time periods shorter than those required to reach equilibrium, as understood by the person skilled in the art. For example, the passive sampler material is impregnated with the PRC prior to insertion in the cage(s) of the PSD of the first aspect. Impregnation is accomplished by inserting the passive sampler material in a PRC composition comprising at least one PRC and at least one PRC solvent, and equilibrating same for the appropriate time, optionally with agitation (for example, stirring, shaking, sonication). The appropriate time for equilibration will be dependent on the passive sampler material, the PRC composition and extent of agitation, as readily understood by the person skilled in the art. It is understood that the "impregnation" can be chemical adsorption and/or physical adsorption.

A fifth aspect of the invention relates to a kit comprising the PSD of the first aspect, with or without the PRC of the fourth aspect. The kit can comprise instructions on how to prepare the PSD for analyte sampling as well as instructions relating to the method of determining the concentration of analyte in the environment to be sampled. The kit can further comprise computer programs to permit the user to calculate the freely dissolved pore water concentrations ($C_{w0}$) of the analyte.

Passive sampling devices often mirror bioaccumulation rates in marine biota and can be useful tools when determining toxicological effects of a local ecosystem. As passive sampler devices are fairly inexpensive, easy to use and small in size, they provide a cost effective alternative or complement to conventionally known grab sampling methods or large volume water extractions currently utilized for most long term water quality monitoring programs.

On the other hand, passive sampling is based on the free flow of an analyte from the sampled medium to a receiving phase in a sampling device. PSDs collect target analyte compounds in situ without affecting the bulk solution. Based on a sampler's design, analysis of the analyte sample may reflect either the concentration with which the device is at equilibrium or the time-averaged concentration to which the sampler was exposed. PSDs are relatively inexpensive, easy to deploy and require minimal monitoring while in situ. Consequently, PSDs have the potential to become reliable and cost-effective tools for monitoring aquatic environments for the presence of pollutants. As a result, PSDs are important in the determination of the concentration of toxic compounds in the environment, remediation design and monitoring, stormwater monitoring, effluent monitoring, and sediment risk assessment.

The features and advantages of the invention are more fully illustrated by the following non-limiting examples, wherein all parts and percentages are by weight, unless otherwise expressly stated.

EXAMPLE 1

Materials

Low density polyethylene (PE) sheets (25 μm thickness), manufactured by Poly-America (Grand Prairie, Tex., USA) were purchased from the Home Depot. PAH and PRC stock solutions were purchased from Fisher Scientific (Pittsburg, Pa., USA). Cylindrical vibrating motors with a diameter of 9 mm and length of 25 mm were purchased from Precision Microdrives (London, United Kingdom). The motors operated at the rated voltage of 3V and operation current of 130 mA. Their rated vibrating speed was 13,500 rpm. Pulse-pause timers (model 60H) were purchased from Velleman Inc. (Fort Worth, Tex., USA). Prior to use, PE sheets were soaked twice in hexane/acetone (50/50) and left on a shaker for 24 h each time to remove residual monomers and any target and non-target contaminants. Clean PE sheets were then cut into 6 mm×2 cm strips (2.8 mg) and were soaked in a PRC solution (80:20 methanol:water with pyrene-d10 and phenanthrene-d10) and allowed to equilibrate for 15 days on an orbital shaker. After impregnation, all strips were removed from the PRC solution and rinsed with DI water to remove the methanol. Two strips were extracted immediately in a 1:1 hexane and acetone mixture (3×24 h) to determine the initial PRC concentration on PE strips.

In-Situ Shaken Passive Sampler Design

Figure 2B:
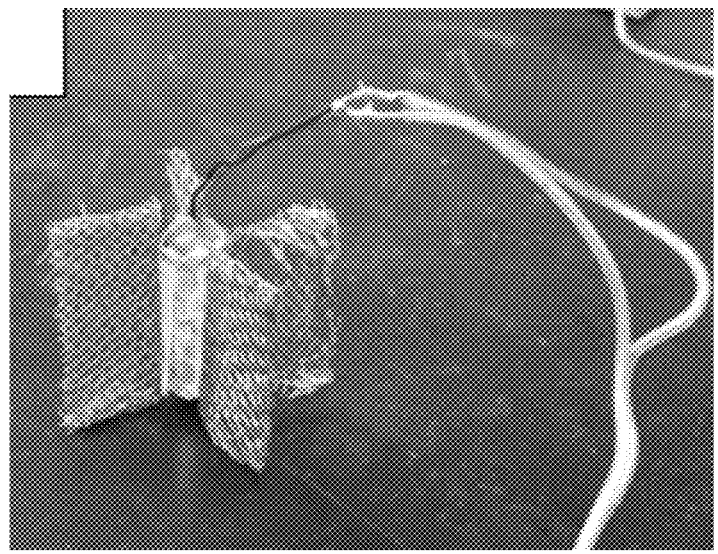
FIG. 2B shows photographs of two adaptations of the vibrating passive sampler where four of the cages of FIG. 2A are attached to a motor like fins.

Two motors were connected in parallel to a timer and a power supply (2 rechargeable batteries 1.2 V, 700 mAh each) (FIG. 1). The timers were powered by a 12 V power supply and were programmed to control motor vibration duration and frequency: 5 seconds pulse and 2 minutes pause (high frequency), 2 seconds pulse and 5 minutes pause (low frequency). The small PE sheets described above were enclosed in stainless steel cages (FIG. 2A) and were attached like radial fins on cylindrical motors (four cages on each motor) as shown in FIG. 2B.

PAH contaminated river sediment samples from the vicinity of former manufactured gas plants studied previously (identified as HD-3 and HD-5 in Khalil, 2006) were used in the present work. The two sediments were combined to obtain sufficient quantity for the present experiments.

The sediment was mixed with DI water containing 200 mg/L sodium azide to make a slurry with weight ratio of 1:2 (dry sediment/water). For the well-mixed exposure, 250 mL of the sediment-water slurry and eight of the prepared PE samplers were transferred to a wide mouth jar with a Teflon-lined lid. The jar was placed on a rotary agitator and tumbled with the speed of 28 rpm. The rest of the sediment slurry was placed in a large glass tray (25 cm×35 cm×6 cm). Four motors were placed inside the sediment in the tray with sufficient separation to prevent influencing each other. Two motors vibrated at the high frequency mode and two at the low frequency mode. Eight additional PE samplers, enclosed in stainless steel cages without motors, were placed inside the same tray in a static mode far from the vibrating motors to simulate a static system. The tray was then covered with aluminum foil. PE strips were removed from the well mixed, static, and vibrating systems and analyzed for native PAHs and PRC compounds after 7, 14, 28 and 56 days. At each time point, two strips were collected from each system and extracted for PAHs analysis.

PAH Extraction and Analysis

Upon removal from the sediment, PE strips were rinsed with water and wiped with laboratory tissue to remove water and adhering particles. Prior to extraction, anthracene-d10 surrogate was added to assess the effectiveness of sample processing, and extracts with lower than 80% surrogate recoveries were discarded. Samplers were extracted with a 1:1 hexane and acetone mixture (3×24 h, with sequential extracts pooled). The final extraction volumes were blown down to 1 mL using a stream of nitrogen gas. PAHs from sediment were extracted by sonication (EPA method 3550B) and cleaned using activated silica gel (EPA method 3630C). Four internal standards were added to the final extracts before analysis (1-fluoronapthalene, p-terphenyl-d14, benzo(a)pyrene-d12, and dibenz(a,h)anthracene-d14). PAHs were analyzed in an Agilent 6890 gas chromatograph coupled to an Agilent 5973N MS detector as described in Khalil (Khalil, 2006).

Modeling Uptake of Analytes from Sediment Pore Water
Static System

Two modeling approaches were taken in order to simulate mass transfer of PAHs from sediment particles into pore water, and from pore water into polymer when the system is in a static mode. The first approach is based on the one dimensional diffusion model presented by Fernandez (Fernandez, 2009). In this model instantaneous equilibrium between sediment particles and pore water is assumed (local equilibrium model). The second approach is based on the assumption that instantaneous equilibrium is not valid and mass transfer from sediment particles into pore water follows the first order kinetics (non-equilibrium sorption). The non-equilibrium sorption model was solved using two different hypotheses: 1) All PAHs are associated with the slow desorbing pool in sediment and desorption is characterized by the slow desorption rate constant; 2) All PAHs are associated with the fast desorbing pool in sediment and desorption is characterized by the fast desorption rate constant.

The slow and fast desorption rate constants for specific PAHs were obtained from desorption kinetics data presented for manufactured gas plant site sediments in Ghosh (Ghosh, 2003).

In a system containing a PE strip with the thickness of $2l_p$ and sediment/pore water with thickness of $l_w$ on both sides, sediment concentration (S) changes as follows:

$$\frac{\partial S}{\partial t} = k(K_d C_w - S) \quad (1)$$

$$l_p < x < l_p + l_w \text{ and } -l_p < x < -l_p - l_w$$

where t is time (s), S is chemical concentration in sediment (ng/gr), $K_d$ is sediment-water partition coefficient (cm$^3$/gr), k is first order desorption rate constant (s$^{-1}$) and $C_w$ is chemical concentration in water (ng/cm$^3$).

For a PE strip with concentration $C_{PE}$ and at point x and time t:

$$\frac{\partial C_{PE}}{\partial t} = D_{PE} \frac{\partial^2 C_{PE}}{\partial x^2} \quad (2)$$

$$-l_p < x < l_p$$

where $C_{PE}$ is chemical concentration in PE (ng/cm$^3$) and $D_{PE}$ is chemical diffusivity in PE (cm$^2$/s).

The transport equation in pore water with concentration of $C_w$ at point x and time t will be as follows:

$$\frac{\partial C_w}{\partial t} = D \frac{\partial^2 C_w}{\partial x^2} - \left(\frac{\rho}{\varepsilon}\right)\frac{\partial S}{\partial t} \quad (3)$$

$$l_p < x < l_p + l_w \text{ and } -l_p < x < -l_p - l_w$$

where $\rho$ is sediment density (gr/cm$^3$) and $\varepsilon$ is porosity (cm$^3$/cm$^3$).

D is the diffusivity in water ($D_w$) after correction for tortuosity:

$$D = \frac{D_w}{1 - \ln \varepsilon^2} \quad (4)$$

Substituting Equation (1) in Equation (3), the transport equation in pore water can be re-written as:

$$\frac{\partial C_w}{\partial t} = D \frac{\partial^2 C_w}{\partial x^2} - \left(\frac{\rho}{\varepsilon}\right) k (K_d C_w - S) \quad (5)$$

Initial Conditions

The polymer was initially clean and pore water was assumed to be in equilibrium with sediment.

$$C_{PE} = 0 \quad -l_p \le x \le l_p \quad (6)$$

$$C_{w0} = S_0/K_d \quad l_p < x < l_p + l_w \text{ and } -l_p < x < -l_p - l_w \quad (7)$$

where $S_0$ is initial chemical concentration in sediment (ng/gr) and $C_{w0}$ is initial chemical concentration in water (ng/cm$^3$).

Boundary Conditions

Continuity of flux and equilibrium condition was assumed at the boundary:

$$D_{PE} \frac{\partial C_{PE}}{\partial x_{PE}} = D \frac{\partial C_w}{\partial x_w} \quad (8)$$

$$x = l_p \text{ and } x = -l_p, t > 0$$

$$C_{PE} = K_{PEw} C_w \quad (9)$$

$$x = l_p \text{ and } x = -l_p$$

where $K_{PEw}$ is the PE-water partition coefficient (cm$^3$/cm$^3$).

Due to symmetry the flux will be zero at the center of the PE sheet. Pore water concentration is equal to the initial concentration far away from the polymer at $x = l_p + l_w$ and does not change over time:

$$\frac{\partial C_{PE}}{\partial x} = 0 \quad (10)$$

$$x = 0$$

$$\frac{\partial C_w}{\partial t} = \frac{\partial S}{\partial t} = 0 \quad (11)$$

$$x = l_p + l_w \text{ and } x = -l_p - l_w$$

Vibrating System

In the vibrating system, when the motor is in pause mode, the mass transfer is similar to the static mode and sediment and pore water concentration in the vicinity of the polymer depletes with time. Every time the motor vibrates, the sediment and pore water in the vicinity of the polymer is mixed up. It was assumed that this mixing is perfect enough to increase sediment concentration to the initial concentration in sediment ($S_0$). Pore water concentration right after each vibration pulse will also increase to the initial concentration:

$$C_w = C_{w0}; S = S_0 \quad l_p < x < l_p + l_w \text{ and } -l_p < x < -l_p - l_w \quad (12)$$

Fully Mixed System

Diffusion in a polymer with thickness of $2l_p$ follows Fick's second law:

$$\frac{\partial C_{PE}}{\partial t} = D_{PE} \frac{\partial^2 C_{PE}}{\partial x^2} \quad (13)$$

$-l_p < x < l_p$

Polymer was assumed to be initially clean. Since the system is perfectly mixed, pore water concentration remains constant and equal to the initial value ($S_0/K_d$) during the deployment time. The boundary condition is defined as:

$$C_{PE}=K_{PEw}C_{w0} \quad x=l_p \text{ and } x=-l_p \qquad (14)$$

The Model equations were solved in Matlab using an explicit, finite-difference numerical modeling technique (Crank, 1975).

PAH Concentration in Sediment and Equilibrium Pore Water

Figure 3:
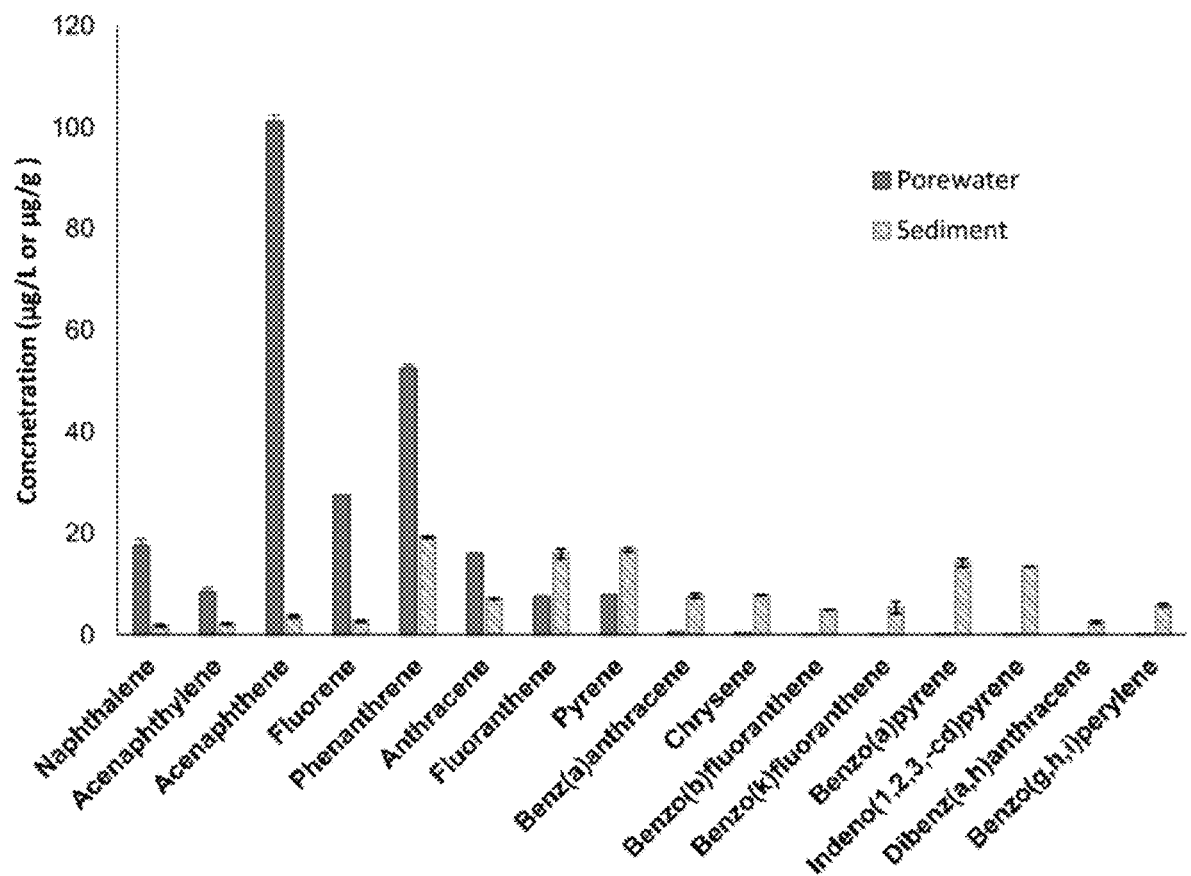
FIG. 3 illustrates the sediment and porewater concentration of sediment used in Example 1.

The concentrations of 16 EPA priority pollutant PAHs in sediment are shown in FIG. 3. The four most abundant PAHs were phenanthrene, fluoranthene, pyrene, and benzo(a)pyrene. The concentration of total PAHs in the sediment was 128 μg/g. The 2-4 ring PAHs comprised 60% of the total in sediment. The equilibrium concentrations in PE ($C_{PE,Eq}$) were determined by extracting the PE samplers after 56 days of deployment in the fully-mixed PE-sediment system. Another time point measurement of PE concentration after 77 days of deployment confirmed that equilibrium had reached in PE for all PAHs in 56 days. Both PRCs (pyrene-d10 and phenanthrene-d10) were depleted completely in the fully-mixed exposure. The freely dissolved pore water concentrations ($C_{w0}$) were calculated from equilibrium concentration of PAHs in PE ($C_{PE,Eq}$) and reported values for $K_{Pew}$ (Lohmann, 2011) (equation 9).

As shown in FIG. 3, PAHs with 2-4 rings contributed to 99% of the total pore water concentration with acenaphthene and phenanthrene showing the highest levels in equilibrium pore water. Toxic units were estimated for each PAH by dividing pore water concentrations by final chronic values (FCVs) (US EPA-600-R-02-012, 2012). The total toxic units of 16 PAHs present in the sediment were approximately 9.33. The fact that the total toxic unit is greater than 1, indicates that PAHs in this sediment likely pose narcosis toxicity to benthic invertebrates (US EPA-600-R-02-012, 2012).

PAH Uptake in Static Deployment

As expected, the uptake of all PAHs was slow in the static exposure. In fact, none of the PAHs from fluoranthene to indeno(1,2,3,-cd)pyrene reached equilibrium in 56 days of contact. The fractional uptake of benz(a)anthracene, benzo(k)fluoranthene and indeno(1,2,3,-cd)pyrene were only 35%, 11%, and 8%, respectively after 28 days. Previous studies have reported similar slow uptake in a static exposure (Fernandez, 2014; Oen, 2011; Tomaszewski, 2008), especially for larger molecular weight compounds. For example, Fernandez (Fernandez, 2014) calculated the fractional equilibration of PCBs into 25 μm PE by measuring the fractional loss of $^{13}$C-labeled PCBs after 44 days of field deployment. The average fractional equilibration of penta- and hexachlorobiphenyls from different points of the field were only 37% and 33%, respectively.

Effect of Vibration on Polymer Uptake Rate

Figure 7A:
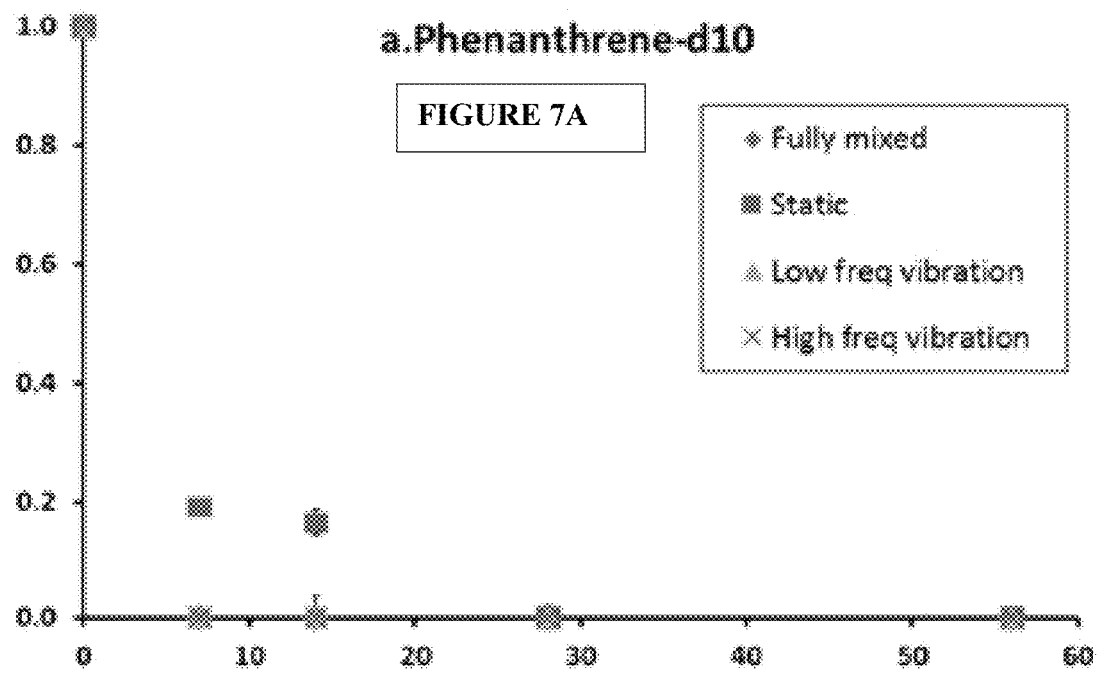
FIG. 7A is a loss profile of deuterated phenanthrene from PE exposed to sediment in a static, low frequency vibration, high-frequency vibration, and fully-mixed system.
Figure 7B:
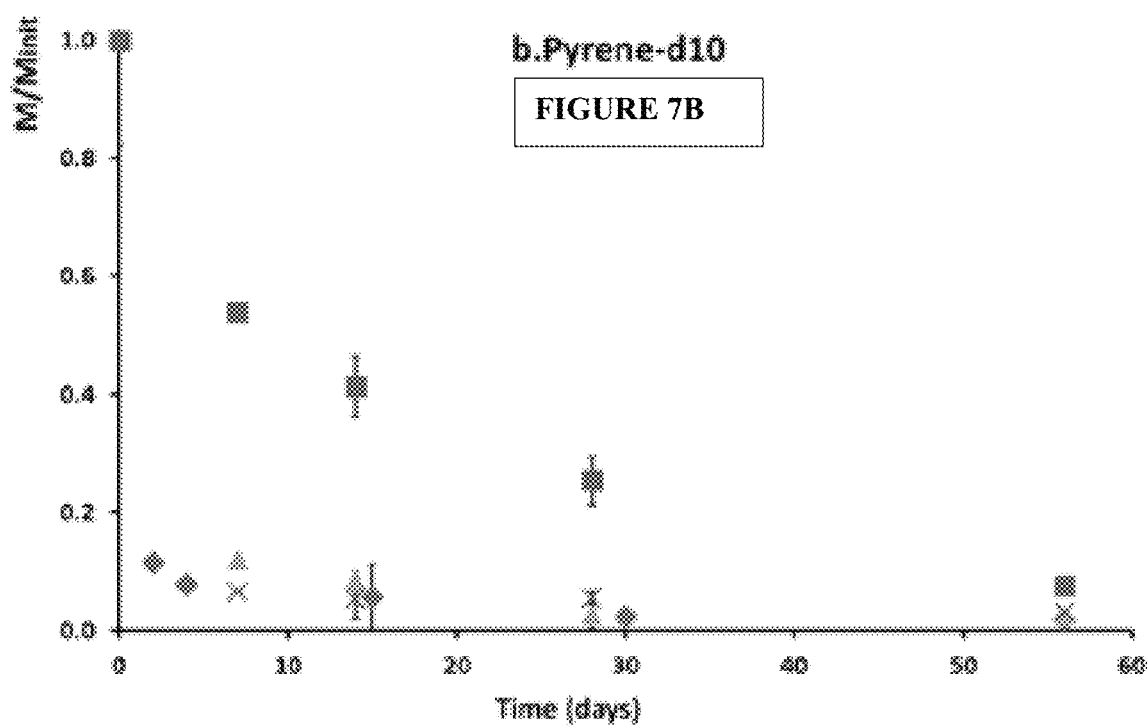
FIG. 7B is a loss profile of deuterated pyrene from PE exposed to sediment in a static, low frequency vibration, high-frequency vibration, and fully-mixed system.

Periodic vibration of the PE sampler resulted in faster uptake compared to static deployment for all PAHs measured. As shown in FIG. 4A, the uptake of chrysene after 56 days was only 40% of equilibrium in static exposure compared to 100% for the vibrating system (see, FIG. 4B). Even after 7 days of exposure, the vibrating system reaches 63% of equilibrium for chrysene compared to 20% in the static system. Comparison between the static and vibrating system for pyrene, chrysene, and benzo(a)pyrene are shown in FIGS. 5A, 5B, and 5C, respectively, and for fluoranthene, benz(a)anthracene, benzo(b)fluoranthene, indeno(1,2,3-cd) pyrene, and benzo(k)fluoranthene are shown in FIGS. 6A, 6B, 6C, 6D, and 6E, respectively. The faster uptake in the vibrating system is mirrored in the faster loss of the PRCs compared to the static system as shown in FIGS. 7A and 7B for phenanthrene-d10 and pyrene-d10, respectively.

For PAH compounds less hydrophobic than chrysene (e.g., fluoranthene (FIG. 6A) and pyrene (FIG. 5A)), the static system showed reasonable uptake of close to 70% in 56 days while the vibrating system reached equilibrium during that exposure. When the passive sampler reaches close to equilibrium, the correction for non-equilibrium is relatively accurate. However, as the kinetics slow down and only a small fraction of equilibrium is achieved in the sampler, the correction for non-equilibrium becomes error-prone. This is the case for the PAH compounds that are more hydrophobic than chrysene. The improvement over static system was more evident for larger molecular weight PAHs. For example, the fractional uptake of benzo(a)pyrene (FIG. 5C) was improved from 6% to 55% in 7 days and from 23% to 90% after 56 days. The fact that vibration was more effective on uptake rate of heavier PAHs can be explained based on the nature of the overall mass transfer resistance in a passive sampler:

$$\frac{1}{k_0} = \frac{\delta}{D_w} + \frac{1}{K_{PEw}D_{PE}} \qquad (15)$$

where $k_0$ is the overall mass transfer rate constant (cm$^2$/s).

The first term on the right hand side of Equation 15, describes the aqueous boundary layer mass transfer resistance. This term is dominant for more hydrophobic compounds which have larger $K_{PEw}$ values. The large $K_{PEw}$ values of the more hydrophobic compounds makes the second term smaller than the first, thereby making the first term or the water side mass transfer more dominant. The ratio of diffusivities in water and polymer ($D_w/D_{PE}$) also increases as the compound becomes more hydrophobic. However, $K_{PEw}$ tends to be the dominant factor controlling which side controls mass transfer since $K_{PEw}$ changes over a wider range of values compared to the range where the diffusivity ratios vary for different compounds (Thompson, 2015). As a result, disrupting the depletion layer (decreasing δ) by means of vibration will be more effective on the overall mass transfer rate of larger molecular weight HOCs. Our experimental data indicated that concentration of larger molecular weight PAHs (log $K_{ow}$>5.5) reached to more than 50% of their equilibrium concentration in PE within 14 days of deployment in the vibrating system (FIGS. 6A-6E). Thus, field deployment of passive samplers using the introduced vibrating system will encounter less challenges of non-equilibrium correction for larger molecular weight compounds.

Results from vibration work demonstrated a great improvement of PE uptake after short exposure times (1-2 weeks). The faster exchange will also allow the use of high molecular weight PRCs to accurately correct for the remaining non-equilibrium in a vibrating system without the need for long exposure times.

Comparison of Three Modeling Approaches in Static, Vibration and Fully-Mixed Deployments FIGS. 4A and 4B also demonstrate modeling results for chrysene in static and vibrating systems based on local equilibrium, slow desorption, and fast desorption models. As shown in FIG. 4A, in static deployment, overall mass transfer into the polymer is slow and the predictions based on local equilibrium assumption and the fast desorption rate model are indistinguishable. Also, both predictions are close to the observed uptake of chrysene in the static deployment. However, the slow rate of desorption model predicts uptake that is slower than the observed values. Thus, it appears that for modeling static deployments, due to the slow rate limiting mass transfer through the static depletion layer, it is adequate to assume local equilibrium between sediment and water.

Figure 8:
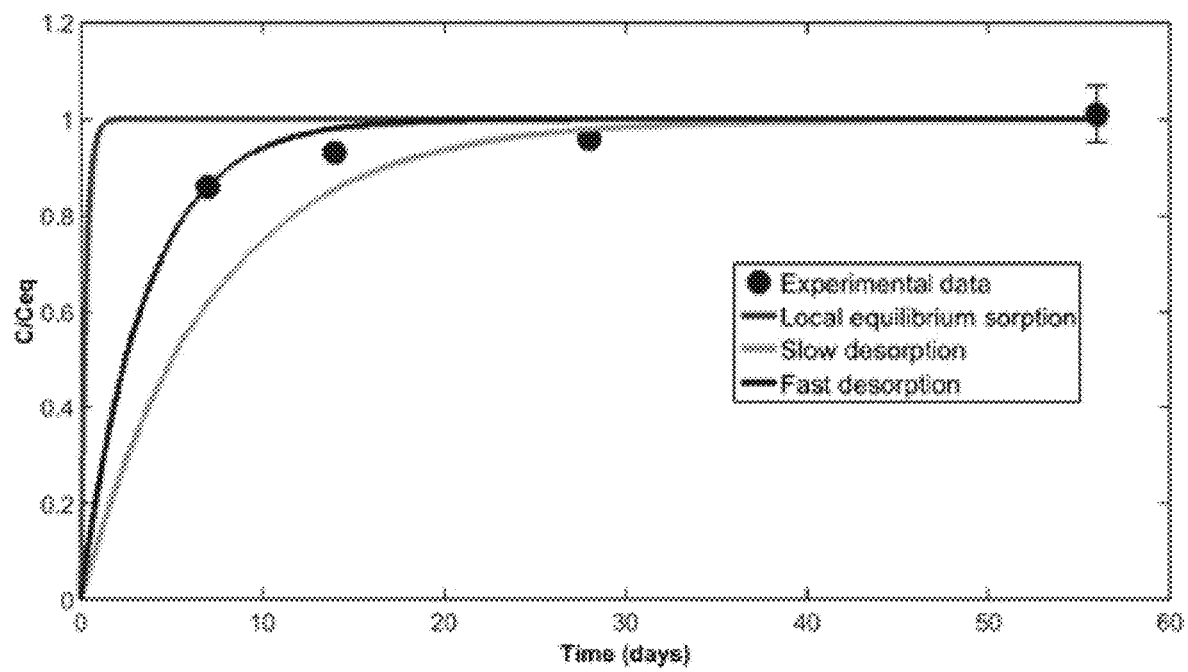
FIG. 8 is comparison of three modeling approaches for the vibrating system of pyrene.

For the vibrating system, the model predictions based on local equilibrium and fast rate of desorption deviated as shown in FIG. 4B. While the fast rate of desorption model prediction is close to the measured uptake of chrysene, the prediction based on local equilibrium greatly over-predicts uptake. The same results were observed for pyrene as indicated in FIG. 8. Thus, it appears that as the depletion layer is disrupted by vibration and mass transfer is enhanced, desorption from sediment becomes limiting and local equilibrium between sediment and water can no longer be assumed. The slow desorption rate still under-predicts uptake in the polymer. Past work has demonstrated that PAH desorption from MGP-impacted sediments are characterized by slow and fast desorbing PAH fractions (Ghosh, 2003). However, the overall kinetics for the vibration system appear to be driven by the fast desorption kinetics and not the slow desorption likely because the sediments are not being depleted enough to reach the slow desorption regime.

For the fully-mixed system, a local-equilibrium model was implemented. As shown in FIG. 4C, the model agrees reasonably with the observed fast uptake of chrysene and the attainment of equilibrium in the matter of a few days. The fully mixed system brings a large volume of sediment to contribute to the required uptake by the passive sampler and hence the kinetics are fast enough to appear close to instantaneous equilibrium.

Modeling Uptake of Pyrene, Chrysene, and Benzo(a)pyrene

Experimental and modeling results for pyrene (log $K_{ow}$=4.9), chrysene (log $K_{ow}$=5.7) and benzo(a)pyrene (log $K_{ow}$=6.1) in static, vibrating, and fully mixed systems are shown in FIGS. 5A-5C, respectively. Based on the discussion above, only the fast desorption model was used for predicting uptake in static and vibrating systems, and a local equilibrium model was used for predicting the fully-mixed system. As shown in FIGS. 5A-5C, the model predictions reasonably agreed with the uptake profiles of the three PAHs in all three modes of exposure. For all three PAHs, although there were some differences between the experimental results from 2 min and 5 min pause times, the model predicted that there should not be much difference between the two. The reason for observing slightly different uptakes in the two frequencies of vibration could be due to different pulse times. Pulse time in the high frequency system (2 min pause) was longer compared to the one in the low frequency system (5 min pause). In the model, we assumed that both pulse durations are long enough to mix up the sediment to initial bulk concentration. However, in reality shorter pulse time (2 seconds) in the low frequency system may not have been long enough to satisfy the model assumption.

To better illustrate how the periodic vibration impacts development of the sediment-side depletion layer, the concentration profiles in the sediment and half width of the PE sampler were plotted for chrysene as a function of exposure time. As shown in FIG. 10A for the static deployment, chrysene in the sediment side is depleted well into 300 μm distance from the PE surface after 20 days. The concentration values for PE plotted in FIGS. 10A and 10B has been multiplied with $K_{sed-PE}$ to make the values directly comparable to the sediment concentration. As indicated in FIG. 10A, the concentration in PE quickly reaches equilibrium with the depleted concentration in the sediment adjacent to the surface and the mass transfer limitation is moved to the 300 micron depleted layer. Also, after the first few hours of exposure, there is no concentration gradient within the polymer indicating all mass transfer resistance is controlled by the sediment side. In stark comparison, for the periodic vibration deployment, since the sediment side is mixed up at frequent intervals, the deep depletion layer in the sediment side is not able to develop and the mass transfer resistance is limited to a few microns near the polymer surface. In fact, as seen in the 2-day simulation for the concentration gradient within PE in the vibrating system, there is still evidence of some polymer-side resistance. As a result, the concentration in PE rises much more rapidly than in the static case.

For the well-mixed system (FIG. 10B), pyrene uptake is fast and modeled reasonably well by the fully mixed local-equilibrium model (FIG. 5A). However, the model is not accurate for early times for the more hydrophobic compounds, especially benzo(a)pyrene (FIG. 5C). This could be due to non-ideal mixing of the system which retards the uptake rate of more hydrophobic compounds. Increasing hydrophobicity also increases dependence on the sediment-side mass transfer limitation as described earlier. Previous studies (Arp, 2015) have observed slower uptake of larger PCBs in well mixed sediment-slurry systems and attributed the kinetics to inefficient mixing and slow desorption.

Optimization of Vibration Frequency

Figure 9:
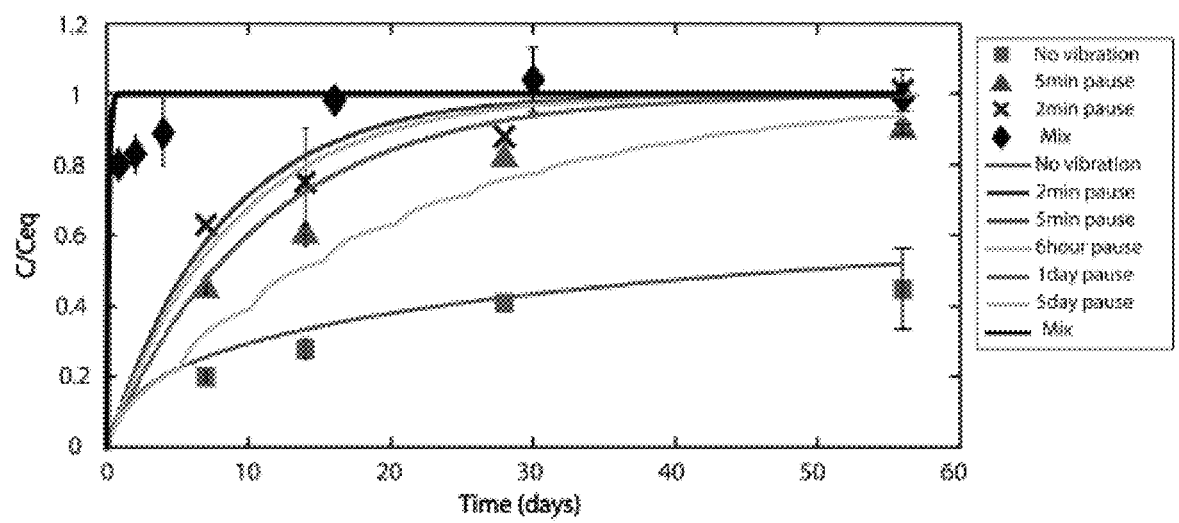
FIG. 9 is a model simulation of chrysene uptake in vibrating system with different pause times of vibration. Experimental data are shown by symbols and fast desorption model simulations are shown by lines.
Figure 11:
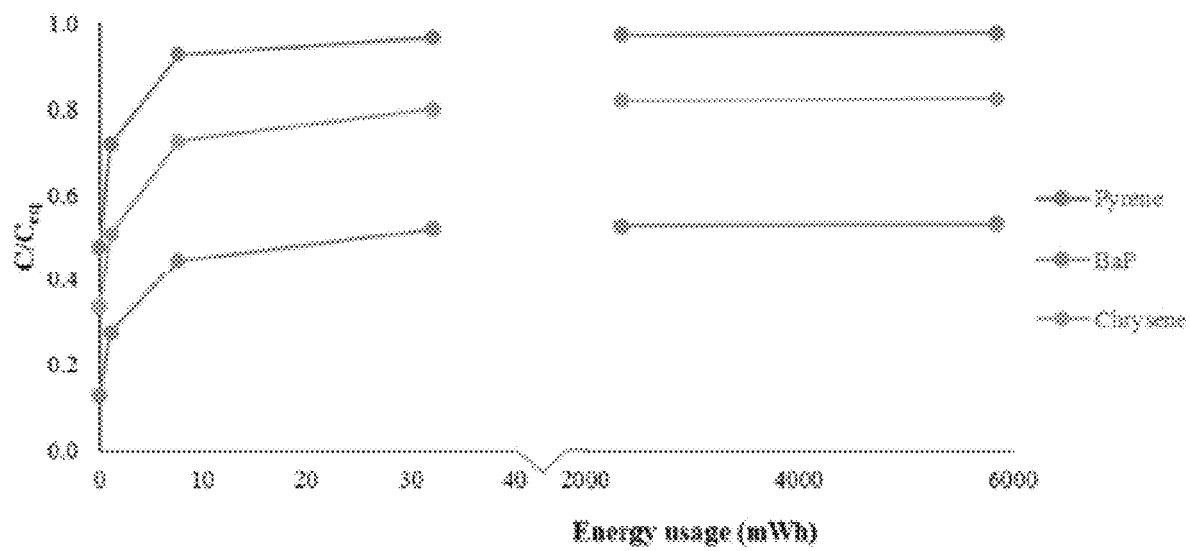
FIG. 11 is a fractional uptake of three PAHs into PE versus energy consumption of one motor after 15 days of deployment.

In order to be able to test the effect of different vibration frequencies and to optimize power requirement, we modeled PE uptake of chrysene under different vibration frequencies. All vibration frequencies had pulse durations of 5 seconds and varied in pause time. The modeling results were based on the fast desorption model and pause times were set as: 2 min, 5 min, 6 hour, 1 day and 5 days (FIG. 9). Small differences were observed between the 2-min and 6-hour pause models. Even the 1-day pause model predicted an uptake kinetic which was not greatly different from the 2 min-pause model. The 5-day pause profile tracked the unmixed profile for the first 5 days, then jumped up to a higher uptake profile as the mixing altered the boundary condition. Although the 5 day-pause model does not show significant improvement over static system in short deployment times (<7 days), the model still predicts 75% fractional uptake after 28 days. In comparison, the fractional uptake of chrysene is only 40% in the static system for the same exposure duration. These results indicate that significant improvement over the static system is possible with lower frequencies of vibration (large pause times). Increasing pause time is desirable as power usage for running the motors will be minimized. In order to optimize pause time, power consumption was estimated for deploying a vibration system for 15 days and a range of pause times. The fractional uptake of three PAHs (pyrene, chrysene and benzo(a)pyrene) in PE after 15 days was also determined with the model for each pause time and plotted versus energy consumption (FIG. 11). According to FIG. 11, only 30 mWh is required to enhance the fractional uptake of chrysene to 80% in 15 days of deployment. In comparison, a typical AA size NiMH rechargeable battery can provide about 1000 mWh of energy. However, further enhancement of fractional uptake in PE from 80% to 82% increases the energy requirement to 2340 mWh. This is also evident from FIG. 9 where we see little enhancement of uptake when the pause time is reduced below 6 hours.

EXAMPLE 2

Materials

Low density polyethylene (LDPE) sheets (25 µm thickness), manufactured by Poly-America (Grand Prairie, Tex., USA), were purchased from The Home Depot (local store in Baltimore, Md.). PCB stock solutions were purchased from Fisher Scientific (Pittsburgh, Pa., USA). Cylindrical vibrating motors with a diameter of 24 mm and length of 31 mm were purchased from Precision Microdrives (London, United Kingdom). The motors operated at the rated voltage of 3 V and operation current of 190 mA. Their rated vibrating speed was 5000 rpm, and the normalized amplitude of vibration (measure of acceleration caused on a 100 g object) was 10 G. Pulse-pause timers (model 60H) used to control the vibration motors were purchased from Velleman Inc. (Fort Worth, Tex.). Prior to use, PE sheets were cleaned by soaking twice in hexane/acetone (50/50 v/v) and leaving on a shaker for 24 h each time. Clean PE sheets were cut into 20 mg (2 cm×5 cm) strips. PE strips were then soaked in a 80:20 v/v methanol/water solution containing four PRCs (2,4,5-trichlorobiphenyl (PCB 29), 2,3',4,6-tetrachlorobiphenyl (PCB 69), 2,2',4,4',6,6'-hexachlorobiphenyl (PCB 155), and 2,3,3',4,5,5',6-heptachlorobiphenyl (PCB 192)). The PRC solution was allowed to equilibrate for 15 days on an orbital shaker. After impregnation with PRCs, the strips were transferred into deionized water and left on an orbital shaker overnight to remove the methanol from PE strips. Upon removal from water, three strips were extracted immediately in hexane to determine the initial PRC concentration.

Source of Sediments

PCB contaminated sediment samples from Site 102 Abraham's Creek were used. The site is located in the Marine Corps Base, Quantico, Virginia, 35 miles south of Washington, D.C., USA.

Vibrating Platform

The vibrating platform has a larger frame and a more powerful motor than that used in Example 1 and as such, could house enough passive sampler to enable measurement of low levels of porewater PCB concentrations in sediment. The platform consisted of a copper pipe section, inside which the motor was located. Four fins made of copper plates and cages were attached radially to the copper pipe. The copper wire cage fins were designed as pockets that could hold PE sheets sandwiched within. A 20 mg PE strip (prepared as discussed above) was placed inside each pocket, and the open edge was sewn with copper wire.

In Situ Vibrated Passive Sampler Setup

Two platforms were connected in parallel to a timer and a power supply (2 rechargeable batteries 1.2 V, 700 mAh each). The timers were powered by a 12 V power supply and were programmed to control motor vibration duration and frequency. Two experiments were conducted in the lab in order to measure the uptake rate of PCBs into PE under different deployment modes. In experiment 1, PE sheets were deployed in sediment under static, mixed, and high frequency vibrating modes. In experiment 2, PE sheets were deployed under static and low frequency vibrating modes. The pulse duration of vibrating motors was 5 s, and the pause period was 2 min and 5 d in the high and low frequency vibrating systems, respectively.

Experiment 1—The sediment was mixed with DI water containing 200 mg/L sodium azide to make a slurry with a weight ratio of 1:2 (dry sediment/water). For the mixed exposure, three wide mouth jars with Teflon-lined lids were prepared. The sediment-water slurry (500 mL) and two of the 20 mg PE samplers were transferred into each jar. The ratio of PE to sediment mass in each jar was selected to reduce PCB depletion from sediment to <1% at equilibrium based on the guideline provided in Ghosh (Ghosh, 2014). The jars were placed on a rotary agitator and tumbled at a speed of 28 rpm. The rest of the sediment slurry was placed in two large glass trays (60 cm×10 cm×10 cm). Three motors were placed inside the sediment in the trays (two of the motors were placed in one tray with 10 cm separation to prevent influencing each other). The timer was programmed to vibrate the motors with a pulse period of 5 s and pause period of 2 min. Twelve additional PE samplers with a mass of 40 mg each were enclosed in stainless steel mesh without motors and were placed inside the same trays in a static mode at least 10 cm away from the vibrating motors and 5 cm apart from each other to simulate a static system. The trays were then covered with aluminum foil. PE strips were removed from the mixed, static, and vibrating systems and analyzed for PCBs and PRC compounds after 7, 14, 28, and 56 days. At each time point, triplicate strips were collected from each system for extraction and analysis.

Experiment 2—PE deployment under static and vibrating modes was repeated in a slurry made with a fresh portion from the same sediment as discussed. This time the motors vibrated with a low frequency of 5 s pulse every 5 days. PE strips were collected in triplicates from static and vibrating systems and analyzed for PCBs after 7, 14, 28, and 56 days.

PCB Extraction and Analysis

Upon removal from the sediment, PE strips were rinsed with water and wiped with laboratory tissue to remove water and adhering particles. Prior to extraction, PCB congeners 14 and 65 were added as surrogate standards to assess the effectiveness of sample processing, and results with lower than 80% surrogate recoveries were discarded. Samplers were extracted in 30 mL of hexane (3×24 h, with sequential extracts pooled). The final extraction volumes were blown down to 1 mL using a stream of nitrogen gas. Sediment PCBs were extracted by sonication (EPA method 3550B). Final extracts from passive samplers and sediment were cleaned using deactivated silica gel (EPA method 3630C). Two internal standards were added to the final extracts before analysis (PCB congeners 30 and 204). PCBs were analyzed in an Agilent 6890N gas chromatograph with an electron capture detector (ECD) based on an analytical method described in Beckingham (Beckingham, 2011).

PCB Desorption Study

The desorption rates of PCBs from sediment into water were measured based on procedures in Beckingham (Beckingham, 2011). Briefly, Tenax beads (0.5 g) and a sediment sample (5 g) were added to 12 mL glass vials. DI water (10 mL) containing sodium azide (1 g/L) was added to each vial. The vials were placed on a rotary agitator and tumbled at 28 rpm. At sampling times of 2, 4, 8, 12, and 48 h the sediment was allowed to settle and Tenax beads to float up. Tenax beads were scooped out from each vial, and a fresh portion was added. The Tenax beads were dried with anhydrous sodium sulfate, spiked with surrogate standards, and extracted by adding three volumes of 15 mL of 50/50 (v/v) hexane-acetone in a 20 mL vial and shaking horizontally on a rotary shaker for 24 h. The final extraction volumes were blown down to 1 mL using a stream of nitrogen gas and were cleaned using deactivated silica gel (EPA method 3630C). The extracts were then analyzed for PCBs using GC-ECD as described above. A two-compartment model (Ghosh, 2001)

was used to describe the desorption kinetics of PCBs from sediment particles into porewater. This model estimates the desorption kinetics of HOCs out of sediment particles based on the assumption that the contaminants are associated with fast and slow desorbing pools in sediment. The model was fitted to the normalized desorption data for PCB 128, 183, and 194 in order to calculate desorption rate constants.

PRC Correction for Nonequilibrium

We used the graphical user interface (GUI) by Tcaciuc to calculate the extent of equilibrium of target PCBs from PRC losses. This GUI is developed based on the mass transfer model presented in Fernandez (Fernandez, 2009). PRC losses in static and vibrating systems were used to determine the extent of equilibrium of target PCBs in the corresponding systems. PCB and PRC concentrations were measured in triplicates, and PRC losses from each PE strip were used to correct for nonequilibrium in the same strip.

Modeling Uptake of Analytes from Sediment Pore Water

The models used for Example 2 are based on the models discussed in Example 1. Briefly, for static deployment mass transfer within the polymer and in porewater was described by Fick's second law of diffusion. Instantaneous equilibrium was assumed at the polymer surface boundary with porewater. PCB desorption from sediment particles into porewater was assumed to follow first-order kinetics, and all PCBs are associated with the fast desorbing pool in sediment. The diffusion model with the assumption of instantaneous equilibrium between sediment particles and porewater (local equilibrium model) adequately predicted the uptake in PE in a static system in Fernandez (Fernandez, 2009).

PCB Concentration in Sediment

Figure 12:
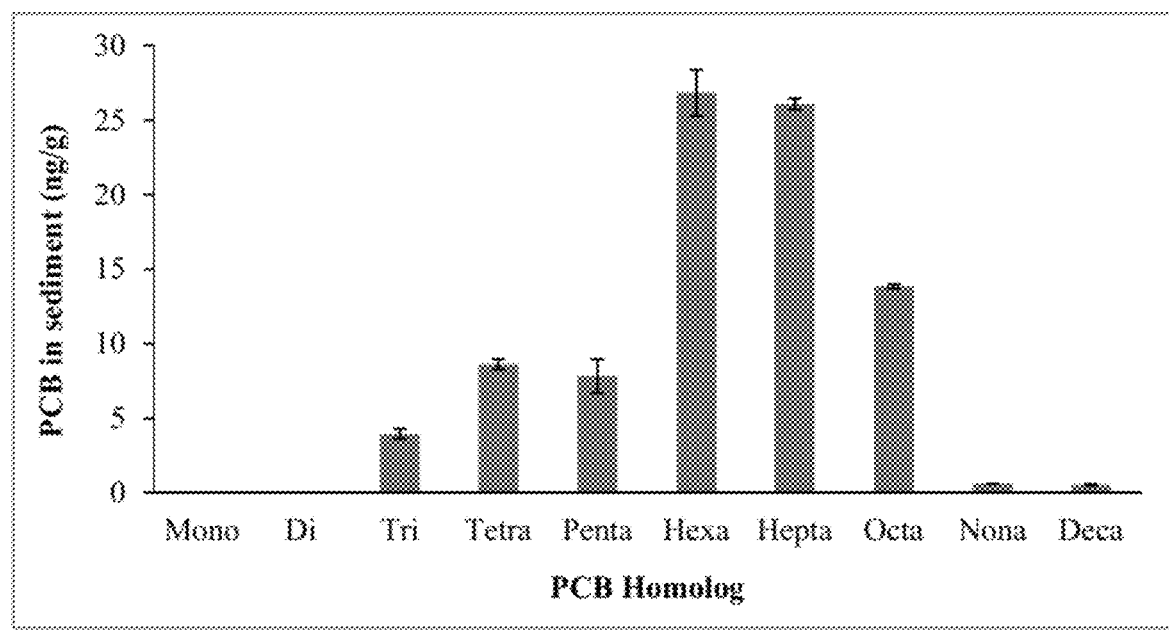
FIG. 12 illustrates the PCB homolog distribution in sediment based on the mean of three measurements. Error bars indicate the mean±one standard deviation (n=3).

As shown in FIG. 12, hexa-, hepta-, and octachloro- PCBs were the most abundant homologues in the sediment. Mono- and dichloro-PCBs were not detected, and the total PCB concentration was 88 ng/g in dry sediment. The sediment had a total organic carbon content of 2.7%.

True Equilibrium Concentration

In the mixed system, no change in concentration in the PE was observed for any of the congeners after 28 days (PE concentrations after 28 and 56 days of exposure were not significantly different). Thus, PCB concentrations in PE from the mixed system after 56 days of exposure were taken as the true equilibrium concentrations for all PCB congeners and used to calculate fraction equilibrium for other modes of deployment.

Effect of High Frequency Vibration on PCB Uptake into PE

The uptake profiles of six PCB congeners are compared in static, vibrated, and mixed systems in FIGS. 13A-13F. The congeners shown in FIGS. 13A-13F were chosen to represent the dominant congener within each homologue group with three to eight chlorine atoms. Since measurements of PCB uptake into PE in the static system from experiments 1 and 2 were not significantly different for all PCBs, only the results from experiment 1 are shown for the static deployment. PCBs had very slow uptake rates into PE in the static exposure system especially for penta- and higher chlorinated PCBs. Periodic vibration of the PE sampler every 2 min enhanced the fractional uptake of all congeners compared to the static deployment. For example, after 28 days of deployment, the fractional uptake (concentration in PE ($C_{PE}$) at a specific time, divided by the true equilibrium $C_{PE}$) of PCB 99 (penta), PCB 153 (hexa), PCB 187+182 (hepta), and PCB 203+196 (octa) were 37%, 24%, 23%, and 22%, respectively, in the static system compared to 100%, 100%, 73%, and 65% in the 2 min-paused vibrating system. All PCBs reached greater than 95% of equilibrium after 56 days of deployment in the 2 min-paused vibrating system, while none of the congeners reached more than 50% of equilibrium in static deployment for the same period. For example, the uptake of PCB 201 after 56 days was only 30% of equilibrium in static exposure compared to 100% in the vibrating system. Even after 7 days of exposure, the vibrating system reaches 35% of equilibrium for PCB 201 compared to 16% in the static system. Thus, with vibration it is apparent that in situ measurements of the full range of PCB congeners in sediments would approach high fraction equilibrium.

Effect of Vibration with Low Frequency on PCB Uptake into PE

The fractional uptake of all PCBs in the 5 d-paused vibrating system improved by a factor of 1.5 to 2 over the static system after 28 days, as shown in FIGS. 13A-13F. However, PCBs reached only 30% to 60% of equilibrium in the 5 d-paused vibrating system, except for PCB 31, PCB 70 +76, and PCB 185 that reached approximately 70%. These results indicate that preferably the pause time between vibrations should be less than 5 days in order to improve the uptake of larger molecular weight PCBs (hexa-, hepta-, and octachloro-congeners) to more than 60% in 28 days.

Effect of Vibration on PRC Loss from PE

The fraction of PRC remaining in PE ($f_{PRC}$) was measured for the four PRCs in static, vibrating, and mixed systems (FIGS. 14A-14D). The fractional losses ($1-f_{PRC}$) of lower molecular weight PRCs PCB 29 and PCB 69 in the static system were 55% and 46%, respectively, after 28 days of deployment. However, both PCBs were 100% dissipated from PE after the same exposure time in the high frequency (2 min-paused) vibrating system. The effect of vibration on PRC loss rate was more evident for PCB 155 and PCB 192. For example, the fractional loss was improved over the static deployment from 22% to 87% for PCB 155 (hexachloro-congener) and from 12% to 63% for PCB 192 (heptachloro-congener) after 28 days. As shown in FIGS. 14A-14D, $f_{PRC}$ for PCB 29 and PCB 69 were nearly identical in high frequency vibrating and mixed exposures. In fact, more than 95% of both PRCs were lost in the vibrating system only after 7 days of exposure. The difference in $f_{PRC}$ between high frequency vibrating and mixed systems was larger for more hydrophobic PRCs (PCB 155 and PCB 192). However, the fractional losses of these PRCs were still reasonably large in the high frequency vibrating system (63% after 28 days and 80% after 56 days for PCB 192).

The measured $f_{PRC}$ values in the static system from experiments 1 and 2 were identical. Thus, only the results from experiment 1 are shown for the static deployment in FIGS. 14A-14D. As indicated in the figures, vibration with low frequency (5 d-paused) was not as effective in improving the dissipation rate of high molecular weight PRCs. For example, the fractional losses of PCB 29 and PCB 69 were increased to approximately 70% after 28 days in the low frequency vibrating system. However, the fractional loss was less than 60% for PCB 155, and the fractional loss was only 25% for PCB 192.

Modeling the Uptake of PCBs

Experimental and modeling results for PCB 128 (hexa), PCB 183 (hepta), and PCB 194 (octa) in static, vibrating, and mixed systems are shown in FIGS. 15A-15C. As described in the modeling section, sediment desorption rate constants are required for the modeling of mass transfer in the vibration system. The measured desorption rate constants ($k_f$) for the three PCB congeners were in the range of 2.4 to 2.8 $d^{-1}$. As shown in FIGS. 15A-15C, modeled uptake in PE generally had good agreement with the measured uptake of all three PCBs in static and vibrating systems with low and high frequency of vibration. This is especially noteworthy because the model uses parameters that have been independently measured or obtained from the literature.

The mixed model overpredicted the earlier time point measurements, likely due to incomplete mixing of the sediment. Deviations between the model simulation and experimental data for the mixed deployment were more obvious for more hydrophobic PCBs (PCB 183 and PCB 194), as mass transfer of these compounds is mostly controlled by the sediment side.

Prediction of Equilibrium Concentration Based on Static vs Shaken Deployment

Measured PCB concentrations in PE using the static and vibration deployments were corrected for nonequilibrium based on the fractional losses of PRCs. PE equilibrium concentrations were also determined from the 56-day mixed deployment. To compare the accuracy of the equilibrium estimations, the estimated $C_{PE}$ values based on PRC-corrected concentrations in PE were compared to the true equilibrium concentrations from the mixed system. In the laboratory mesocosms with static overlying water, we expect that PCBs in porewater approach thermodynamic equilibrium with the sediment. Thus, porewater concentrations measured in the "mixed equilibrium exposures" should closely represent the true equilibrium porewater concentration to be expected in the static and vibrating passive sampler deployments. The PRC-corrected $C_{PE}$ values measured with 7- and 28-day static and vibrated passive samplers are plotted in FIGS. 16 and 17, respectively, and compared against the true equilibrium $C_{PE}$ values. In both figures, the PRC-corrected $C_{PE}$ values that are statistically different from the true values (with alpha level of 5%) are indicated with asterisks.

Figure 16A:
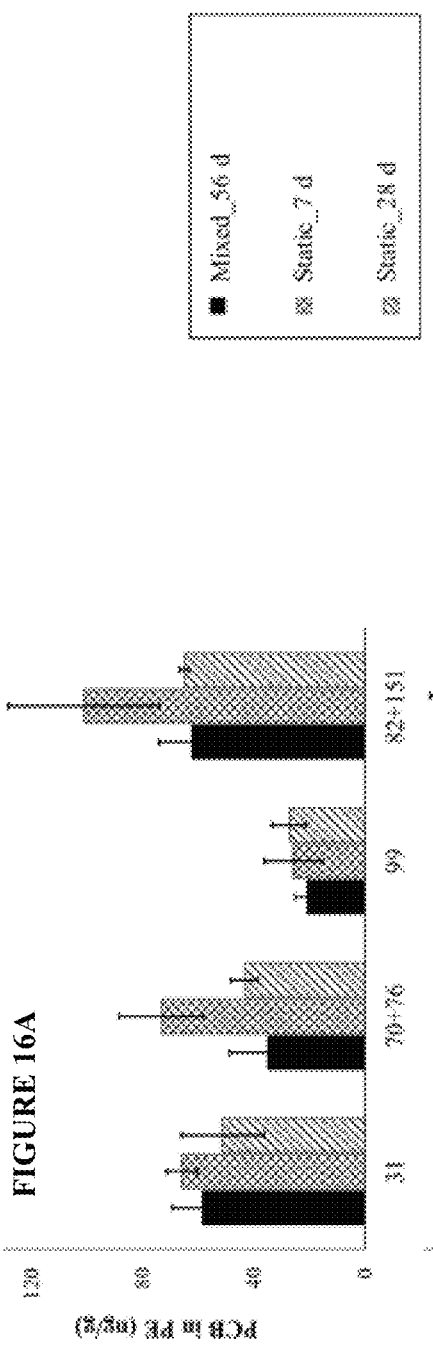
FIG. 16A is a comparison of 56-day mixed (true) equilibrium concentration in PE with PRC-corrected PE equilibrium concentration measured using 7-day and 28-day static exposures. The PCB congeners belong to pentachloro- and lower molecular weight congeners. The corrected concentrations that are statistically different from the 56-day mixed equilibrium concentrations (with alpha level of 5%) are indicated with an asterisk. Error bars represent the mean±one standard deviation (n=3).
Figure 16B:
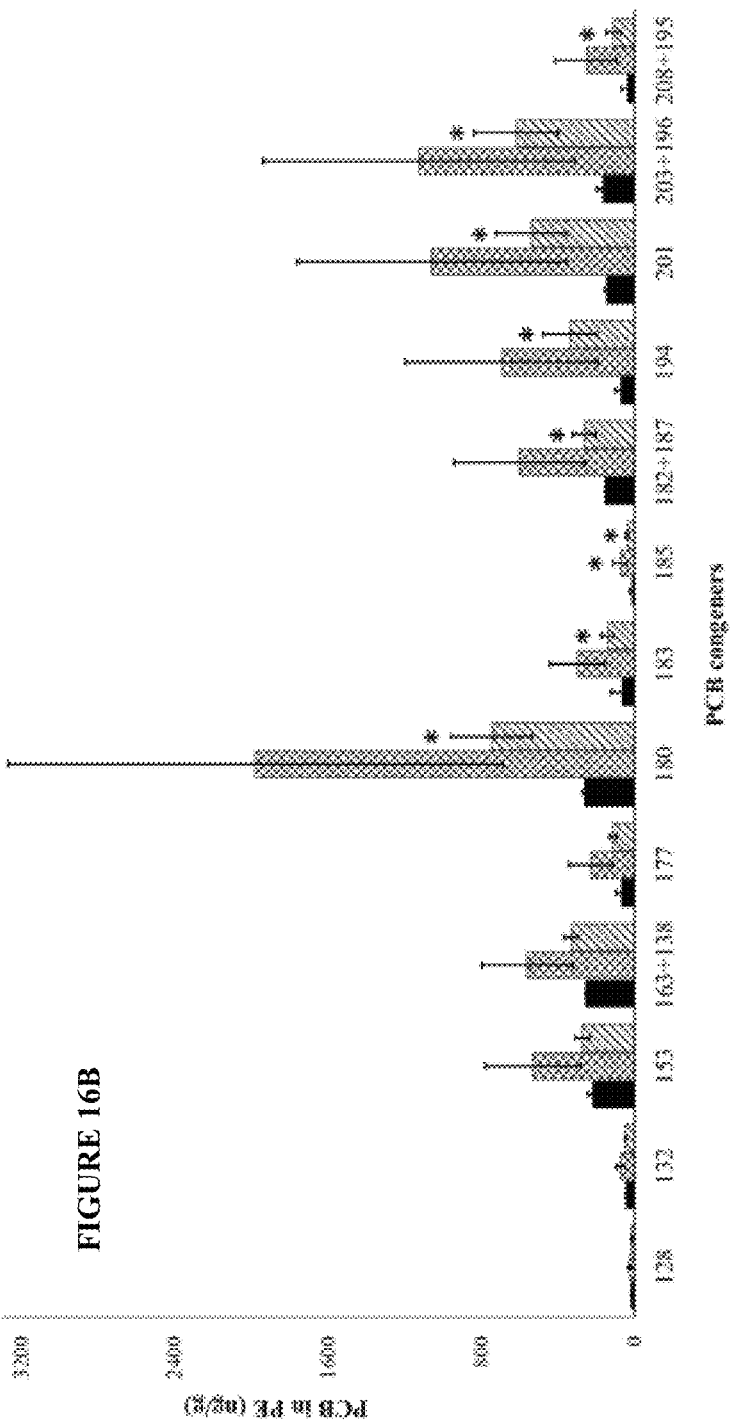
FIG. 16B is a comparison of 56-day mixed (true) equilibrium concentration in PE with PRC-corrected PE equilibrium concentration measured using 7-day and 28-day static exposures. The PCB congeners belong to hexachloro- and higher molecular weight congeners. The corrected concentrations that are statistically different from the 56-day mixed equilibrium concentrations (with alpha level of 5%) are indicated with an asterisk. Error bars represent the mean±one standard deviation (n=3).

As shown in FIG. 16, the tri-, tetra-, and pentachloro-congeners (PCB 31, 70 +76, 99, and 82+151) are generally well-predicted by the static passive samplers (within a factor of 2) for both 7-day and 28-day deployments. For these moderately hydrophobic congeners, the PRC losses are high in both deployment durations, and correction for nonequilibrium is relatively accurate. The measurements using static deployment start deviating strongly for the higher chlorinated PCBs (hexa and higher). There appears to be a consistent positive bias for the estimation from static deployment. For example, equilibrium $C_{PE}$ for PCB 180 is predicted to be 7.7-fold higher from the 7-day deployment and 2.9-fold higher from the 28-day deployment. As expected, $C_{PE}$ estimations using the 7-day deployment data in the static system were less accurate compared to the estimations using 28-day deployment data, especially for higher molecular weight PCBs. The error bars are also large, indicating poor precision. Many of the equilibrium $C_{PE}$ prediction for the static deployment have large deviation from the true equilibrium $C_{PE}$ (e.g., up to a factor of 10 for 7-day deployment) but often do not show statistically significant difference due to the very large associated error of the estimation. The predictions improve with length of deployment but remain poor with a factor of 5 overprediction for several hepta- and octachloro-PCBs.

As shown in FIG. 17, the PRC-corrected $C_{PE}$ values from the 2 min-paused vibration deployment are much more accurate and precise compared to measurements from the static deployment. For example, the estimated equilibrium $C_{PE}$ for PCB 180 is 291 and 346 ng/g after 7 and 28 days of deployment in the 2 min-paused vibration system, respectively. That means, equilibrium $C_{PE}$ of PCB 180 is predicted within a factor of 1.1 of the true value of 258 ng/g even after a 7-day deployment. Even PCB 208+195, which are the most hydrophobic congeners measured, are predicted within a factor of 1.2 after 7 days deployment despite the fact that only 40% of the equilibrium concentration was reached. Both 7-day and 28-day deployments of the 2 min-paused vibrating system yield close to the true value for all measured PCBs.

Increasing pause time to 5 days made the equilibrium $C_{PE}$ measurements less accurate than the 2 min pause vibration but was better than the static deployments. For example, $C_{PE}$ for PCB 180 was predicted within a factor of 1.9 by the 5-d-paused deployment in 28 days compared to a factor of 2.9 for the same deployment period for the static system. Thus, even a very intermittent vibration can greatly enhance the accuracy of the $C_{PE}$ measurement. Higher precisions in estimation of $C_{PE}$ using the low frequency vibration deployment results in estimated equilibrium concentrations that are statistically different from the true values, yet the absolute values are closer to the true value compared to the static deployment.

Since passive sampling is often used to estimate $C_{free}$, PCB concentrations in PE were converted to $C_{free}$ using the individual congener PE-water partition constants ($K_{PEw}$). The $K_{PEw}$ values for PCB congeners were estimated from the correlation provided in Ghosh (Ghosh, 2014). Conversion to $C_{free}$ values appears to reduce the contribution of the highly chlorinated congeners toward the total PCB $C_{free}$. In this study, we did not see significant differences between the PRC-corrected and true equilibrium $C_{PE}$ of hexachloro- and lower molecular weight PCBs for the 28 d-deployment time. In fact, the differences were significant for high molecular weight PCBs (some of the hepta-, and all octa-, and nonachloro congeners) (FIG. 16).

The results of Example 2 were that the PRC corrections were not reliable for estimating sediment porewater concentrations of strongly hydrophobic PCBs during a typical deployment time. That said, the introduction of periodic vibration greatly enhances the time to equilibrium, increases measurement accuracy, reduces deployment times, and extends the use of passive sampling in conjunction with PRCs to strongly hydrophobic compounds. With periodic vibration, even a 7-day deployment is adequate for a reasonably accurate in situ measurement of $C_{free}$ for all PCB compounds. Shorter deployment times reduce the risk of loss, destruction, and vandalism of deployed passive sampler platforms in the field and can reduce costs when deployment and retrieval may be performed in one mobilization to the field. Using periodic vibration for a longer deployment of a month, it may even be possible to reach so close to equilibrium that PRC corrections may not be necessary for many compounds.

Although the invention has been variously disclosed herein with reference to illustrative embodiments and features, it will be appreciated that the embodiments and features described hereinabove are not intended to limit the invention, and that other variations, modifications and other embodiments will suggest themselves to those of ordinary skill in the art, based on the disclosure herein. The invention therefore is to be broadly construed, as encompassing all such variations, modifications and alternative embodiments within the spirit and scope of the claims hereafter set forth.

REFERENCES

Apell, J. N., Gschwend, P. M. Validating the use of performance reference compounds in passive samplers to assess porewater concentrations in sediment beds. *Environ. Sci. Technol.* 2014, 48. 10301-10307.

Arp. H. P. H., Hale, S. E., Elmquist Krusa, M., Cornelissen, G., Grabanski, C. B., Miller, D. J., Hawthorne. S. B. Review of polyoxymethylene passive sampling methods for quantifying freely dissolved porewater concentrations of hydrophobic organic contaminants. *Environ. Toxicol. Chem.* 2015, 34, 710-720.

Beckingham, B., Ghosh, U. Field-scale reduction of PCB bioavailability with activated carbon amendment to river sediments *Environ. Sci. Technol.* 2011, 45 (24) 10567-10574.

Booij. K., Hoedemaker, J. R., Bakker. J. F. Dissolved PCBs, PAHs, and HCB in Pore Waters and Overlying Waters of Contaminated Harbor Sediments. *Environ. Sci. Technol.* 2003, 37 (18), 4213-4220.

Booij, K., Smedes, F. An improved method for estimating in situ sampling rates of nonpolar passive samplers. *Environ. Sci. Technol.* 2010, 44, 6789-6794.

Booij, K., Robinson, C. D., Burgess, R. M., Mayer, P., Roberts, C. A., Ahrens, L., Allan. L I., Brant, J. Jones, L., Kraus, U. R., Larsen, M. M., Lepom. P., Petersen, J., Profrock, D., Roose, P., Schafer, S., Smedes, F., Tixier, C., Vorkamp, K., Whitehouse, P. Passive Sampling in Regulatory Chemical Monitoring of Nonpolar Organic Compounds in the Aquatic Environment. *Environ. Sci. Technol.* 2015. 50, 3-17.

Cornelissen, G., Van Noort, P. C. M., Govers, H. A. J. Desorption kinetics of chlorobenzenes, polycyclic aromatic hydrocarbons, and polychlorinated biphenyls: Sediment extraction with Tenax and effects of contact time and solute hydrophobicity *Environ. Toxicol. Chem.* 1997, 16, 1351-1357.

Crank, J. *The Mathematics of Winston*, 2$^{nd}$ ed.; Oxford University Press: Oxford, 1975; p 414.

Fernandez, L. A., Harvey, C. F. and Gschwend, P. M. Using Performance Reference Compounds in Polyethylene Passive Samplers to Deduce Sediment Porewater Concentrations for Numerous Target Chemicals. *Environ. Sci. Technol.* 2009, 43, 8888-8894.

Fernandez, L. A., Lao, W., Maruya, K. A., Burgess, R. M. Calculating the Diffusive Flux of Persistent Organic Pollutants between Sediments and the Water Column on the Palos Verdes Shelf Superfund Site Using Polymeric Passive Samplers. *Environ. Sci. Technol.* 2014.48 (7), 3925-3934.

Ghosh, U., Talley, J. W., Luthy, R. G. Particle-scale investigation of PAH desorption kinetics and thermodynamics from sediment *Environ. Sci. Technol.* 2001, 35, 3468-3475.

Ghosh, U., Zimmerman, J. R., and Luthy, R. G. PCB and PAH Speciation among Particle Types in Contaminated Harbor Sediments and Effects on PAH Bioavailability. *Environ. Sci. Technol.* 2003. 37. 2209-2217.

Ghosh, U., Kane Driscoll, S., Burgess, R. M., Jonker, M. T. 0., Reible, D., Gobas, F., Choi, Y., Apitz, S. E., Maruya, K. A., Gala, W. R., Mortimer, M. and Beegan, C. Passive sampling methods for contaminated sediments: Practical guidance for selection, calibration, and implementation: *Integr Environ Assess Manag.* 2014, 10, 210-223.

Hawthorne, S. B., Grabanski, C. B., Miller, D. J. Measured partitioning coefficients for parent and alkyl polycyclic aromatic hydrocarbons in 114 historically contaminated sediments: Part 1. KOC values. *Environ. Toxicol. Chem.* 2006, 25, 2901-2911.

Huckins, J. N., Petty, J. D., Lebo, J. A., Almeida, F. V., Booij, K., Alvarez, D. A., Clark, R. C., Mogensen, B. B. Development of the permeability/performance reference compound approach for in situ calibration of semipermeable membrane devices. *Environ. Sci. Technol.* 2002, 36 (1), 85-91.

Huckins, J. N., Petty J. D., Booij, K. *Monitors of Organic Chemicals in the Environment*; Springer: New York, N.Y., 2006.

Khalil. M. F., Ghosh, U. and Kreitinger, J. P. Role of Weathered Coal Tar Pitch in the Partitioning of Polycyclic Aromatic Hydrocarbons in Manufactured Gas Plant Site Sediments. *Environ. Sci. Technol.* 2006, 40, 5681-5687.

Lampert, D. An assessment of the design of in situ management approaches for contaminated sediments. Ph.D. Thesis, The University of Texas at Austin, May 2010.

Lohmann, R. Critical Review of Low-Density Polyethylene's Partitioning and Diffusion Coefficients for Trace Organic Contaminants and Implications for Its Use as a Passive Sampler. *Environ. Sci. Technol.* 2011, 46, 606-618.

Mayer, P., Tolls, J., Hermens, J. L. M. and Mackay, D. Equilibrium Sampling Devices. *Environ. Sci. Technol.* 2003, 37, 184A-191A.

Mayer, P., Parkerton, T. F., Adams, R. G., Cargill, J. G., Gan, J., Gouin, T., Gschwend, P. M., Hawthorne, S. B., Helm, P., Witt, G., You, J. and Escher, B. I. Passive sampling methods for contaminated sediments: Scientific rationale supporting use of freely dissolved concentrations. *Integr Environ Assess Manag.* 2014, 10, 197-209.

Oen, A. M. P., Janssen, E. M. L., Cornelissen, G., Breedveld, G. D., Eek, E. and Luthy, R. G. In Situ Measurement of PCB Pore Water Concentration Profiles in Activated Carbon-Amended Sediment Using Passive Samplers. *Environ. Sci. Technol.* 2011, 45, 4053-4059.

Tcaciuc, A. P., Apell, J. N., Gschwend, P. M. Performance Reference Compound Calculator for Use in Support of PE Passive Samplers. http://www.serdp .org/Program-Areas/Environmental-Restoration/Contaminated-Sediments/ER-200915 (accessed May 30, 2017).

Thompson, J., Hsieh, C., and Luthy, R. G. Modeling Uptake of Hydrophobic Organic Contaminants into Polyethylene Passive Samplers. *Environ. Sci. Technol.* 2015, 49 (4), 2270-2777.

Tomaszewski, J., Lutly, R. G. Field deployment of polyethylene devices to measure PCB concentrations in pore water of contaminated sediment. *Environ. Sci. Technol.* 2008, 42 (16), 6086-6091.

United States Environmental Protection Agency. Equilibrium Partitioning Sediment Benchmarks (ESBs) for the Protection of Benthic Organisms: Procedures for the Determination of the Freely Dissolved Interstitial Water Concentrations of Nonionic Organics. EPA-600-R-02-012. Office of Research and Development, Washington, D.C., USA, 2012.

What is claimed is:

1. A passive sampling device (PSD) comprising at least one cage and at least one vibrating device, wherein at least one passive sampler is in each cage.

2. The PSD of claim 1, wherein the at least one cage is in direct contact with the at least one vibrating device.

3. The PSD of claim 1, further comprising at least one pulse-pause timer.

4. The PSD of claim 1, wherein the at least one cage can comprise a pocket which the passive sampler can be inserted into.

5. The PSD of claim 1, wherein the cage comprises metal, polymer, or a combination thereof, and is substantially resistant to corrosion in an environment to be tested, and is durable enough to be placed in an environment to be tested.

6. The PSD of claim 5, wherein the cage comprises copper, stainless steel, or alloys comprising copper, nickel, and/or chromium.

7. The PSD of claim 1, wherein the cage is open to the environment for the flow of analyte into and out of the cage.

8. The PSD of claim 1, wherein at least one passive sampler comprises a material selected from the group consisting of silicone rubber, low-density polyethylene (LDPE), polyethylene (PE), polyoxymethylene (POM), polydimethylsiloxane (PDMS), polyethersulfone (PES), and polyacrylate (PA), optionally impregnated with a performance reference compound.

9. A method of determining the amount of an analyte in an environment, said method comprising:
(a) positioning a PSD in the environment for time x, wherein the PSD comprises at least one cage and at least one vibrating device, wherein at least one passive sampler is in each cage;
(b) removing the PSD from the environment at the end of time x and removing the passive sampler material(s) from the cage(s);
(c) extracting the analyte from the passive sampler material using at least one extraction solvent; and
(d) calculating the amount of analyte collected in the PSD and optionally, making corrections for non-equilibrium.

10. The method of claim 9, further comprising vibrating the PSD during time x for at least one time y.

11. The method of claim 10, further comprising pausing the vibrations of the PSD for at least a time z.

12. The method of claim 11, further comprising (e) vibrating the PSD during time x for at least one time y, and (f) pausing the vibrations of the PSD for at least a time z, in a range from at least 1 to at least 1000 times during time x.

13. The method of claim 9, wherein the amount of analyte collected in the PSD corresponds to an equilibrium concentration or less than the equilibrium concentration.

14. The method of claim 9, comprising the step of making corrections for non-equilibrium, said step comprising impregnating the passive sampler with a performance reference compound (PRC), calculating the amount of PRC in the passive sampler at the end of time x, and calculating the amount of analyte corresponding to an equilibrium concentration.

15. The method of claim 13, wherein the equilibrium concentration is used to calculate a freely dissolved pore water concentration ($C_{w0}$) of the analyte.

16. The method of claim 14, wherein the equilibrium concentration is used to calculate a freely dissolved pore water concentration ($C_{w0}$) of the analyte.

17. The method of claim 10, wherein the time y is in a range from about 1 second to about 60 seconds.

18. The method of claim 17, wherein the time y is in a range from about 1 second to about 10 seconds.

19. The method of claim 11, wherein the time z is in a range from about 1 minute to about 1 day.

20. The method of claim 19, wherein the time z is in a range from about 2 minutes to about 10 minutes.

* * * * *